(12) United States Patent
Carbonelli et al.

(10) Patent No.: US 11,187,647 B2
(45) Date of Patent: Nov. 30, 2021

(54) SYSTEM AND METHOD FOR ESTIMATING A GAS CONCENTRATION

(71) Applicant: Infineon Technologies AG, Neubiberg (DE)

(72) Inventors: Cecilia Carbonelli, Munich (DE);
Renato Bessegato, Oberhaching (DE);
Wolfgang Furtner, Fuerstenfeldbruck (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 0 days.

(21) Appl. No.: 16/879,152

(22) Filed: May 20, 2020

(65) Prior Publication Data
US 2020/0300756 A1 Sep. 24, 2020

Related U.S. Application Data

(62) Division of application No. 16/240,187, filed on Jan. 4, 2019, now Pat. No. 10,712,264.
(Continued)

(51) Int. Cl.
| G01N 21/17 | (2006.01) |
| G01N 29/24 | (2006.01) |
| G01N 29/32 | (2006.01) |
| G01N 29/42 | (2006.01) |
| G01N 29/46 | (2006.01) |
(Continued)

(52) U.S. Cl.
CPC ..... *G01N 21/1702* (2013.01); *G01N 21/3504* (2013.01); *G01N 29/2418* (2013.01); *G01N 29/32* (2013.01); *G01N 29/343* (2013.01); *G01N 29/42* (2013.01); *G01N 29/46* (2013.01); *G01N 33/004* (2013.01); *G10K 11/17853* (2018.01); *G10K 11/17883* (2018.01); *G01N 2021/1704* (2013.01); *G01N 2291/021* (2013.01);
(Continued)

(58) Field of Classification Search
None
See application file for complete search history.

(56) References Cited

U.S. PATENT DOCUMENTS

| 4,051,371 A | 9/1977 | Dewer, Jr. et al. |
| 4,622,845 A | 11/1986 | Ryan et al. |
(Continued)

FOREIGN PATENT DOCUMENTS

| EP | 2518473 A1 | 10/2012 | |
| WO | WO-2007004168 A1 * | 1/2007 | ............ G01N 21/39 |

OTHER PUBLICATIONS

Chansin, Guillaume Dr., et al., "Environmental gas sensors 2017-2027—Technologies, manufacturers, forecasts", IDTechEx.com, Jan. 17, 2017, 217 pages.
(Continued)

*Primary Examiner* — Thomas R Artman
(74) *Attorney, Agent, or Firm* — Slater Matsil, LLP

(57) ABSTRACT

In accordance with an embodiment, a method of measuring a gas concentration includes modulating an infrared light source according to a frequency-hopped sequence or according to a pulse sequence, receiving a microphone signal from an output of a microphone acoustically coupled to a gas exposed to infrared light produced by the infrared light source; bandpass filtering the microphone signal using a bandpass filter; and estimating the gas concentration from the filtered microphone signal.

20 Claims, 15 Drawing Sheets

Related U.S. Application Data

(60) Provisional application No. 62/614,077, filed on Jan. 5, 2018.

(51) Int. Cl.
  *G01N 21/3504* (2014.01)
  *G01N 33/00* (2006.01)
  *G01N 29/34* (2006.01)
  *G10K 11/178* (2006.01)

(52) U.S. Cl.
  CPC .............. *G01N 2291/02809* (2013.01); *G10K 2210/3028* (2013.01)

(56) References Cited

U.S. PATENT DOCUMENTS

| | | | |
|---|---|---|---|
| 5,373,160 A | 12/1994 | Taylor | |
| 5,451,787 A | 9/1995 | Taylor | |
| 5,780,724 A * | 7/1998 | Olender | G01M 3/38 73/24.01 |
| 5,824,884 A | 10/1998 | Olender et al. | |
| 6,608,683 B1 | 8/2003 | Pilgrim et al. | |
| 6,618,148 B1 | 9/2003 | Pilgrim et al. | |
| 7,034,943 B1 | 4/2006 | Moeckli et al. | |
| 7,263,871 B2 | 9/2007 | Selker et al. | |
| 7,304,742 B1 | 12/2007 | Gurton | |
| 7,398,672 B2 | 7/2008 | Riddle | |
| 7,765,871 B2 | 8/2010 | Riddle | |
| 7,797,983 B2 | 9/2010 | Kauppinen | |
| 8,085,403 B2 | 12/2011 | Fritz et al. | |
| 8,312,758 B2 | 11/2012 | Tobias | |
| 8,434,366 B2 | 5/2013 | Hung et al. | |
| 8,451,447 B2 | 5/2013 | Fritz et al. | |
| 8,561,454 B2 | 10/2013 | Muehleisen | |
| 9,696,283 B1 * | 7/2017 | Yu | G01N 29/2418 |
| 9,752,931 B2 | 9/2017 | Waldmann et al. | |
| 10,712,264 B2 * | 7/2020 | Carbonelli | G01N 33/004 |
| 2006/0123884 A1 | 6/2006 | Selker et al. | |
| 2007/0151325 A1 | 7/2007 | Kauppinen | |
| 2008/0011055 A1 | 1/2008 | Riddle | |
| 2008/0134756 A1 | 6/2008 | Riddle | |
| 2009/0320561 A1 | 12/2009 | Fritz et al. | |
| 2010/0027012 A1 | 2/2010 | Fritz et al. | |
| 2010/0045998 A1 | 2/2010 | Fritz et al. | |
| 2012/0075618 A1 | 3/2012 | Fritz et al. | |
| 2012/0151994 A1 | 6/2012 | Hung et al. | |
| 2015/0092194 A1 | 4/2015 | Waldmann et al. | |
| 2019/0212259 A1 | 7/2019 | Carbonelli et al. | |
| 2020/0300756 A1 * | 9/2020 | Carbonelli | G01N 29/2418 |

OTHER PUBLICATIONS

Fazel, K. et al., "Multi-Carrier and Spread Spectrum Systems," From OFDM and MC-CDMA to LTE and WiMAX, Second Edition, Wiley, Dec. 2003, 379 pages.

Huber, Jochen et al., "Simulation model for the evaluation and design of miniaturized non-resonant photoacoustic gas sensors", J. Sens. Sens. Syst., 5, Jul. 2016, pp. 293-299.

"High-Resolution spectral modeling," SpectralCalc.com, printed Jan. 4, 2019, 1 page.

\* cited by examiner

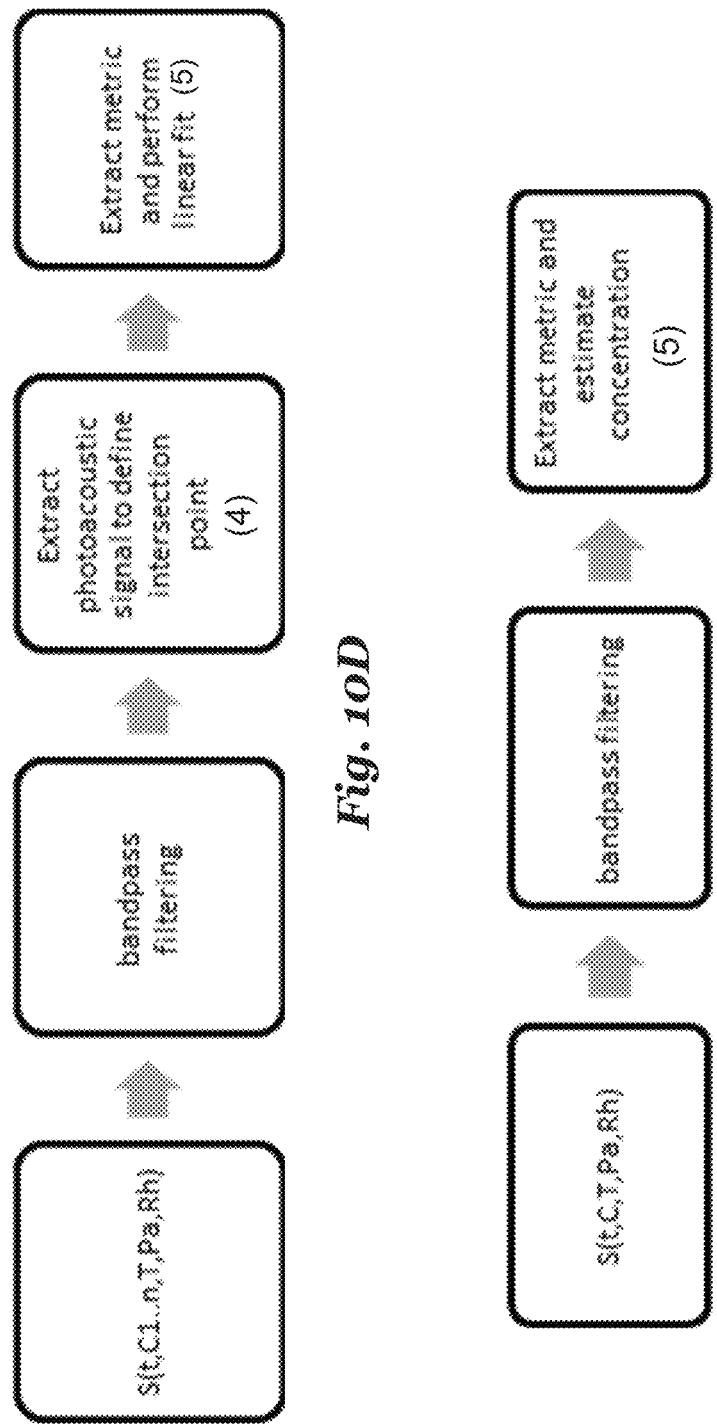

SYSTEM AND METHOD FOR ESTIMATING A GAS CONCENTRATION

This application is a divisional of U.S. patent application Ser. No. 16/240,187, filed Jan. 4, 2019, which application claims the benefit of U.S. Provisional Application No. 62/614,077, filed on Jan. 5, 2018, which applications are hereby incorporated herein by reference in its entirety.

TECHNICAL FIELD

The present invention relates generally to a system and method, and, in particular embodiments, to a system and method for measuring a gas concentration.

BACKGROUND

Applications for gas sensors have gained significant interest in the past few years due to growing concerns over air pollution and global climate change. For example, carbon dioxide sensors are commonly used to measure machine emissions and indoor air quality. There are a number of general methods of measuring a gas concentration. A chemical sensor measures a gas concentration by measuring an electrical property of a gas sensitive material, such as a metal oxide (MOX) or graphene. On the other hand, a physical sensor measures a gas concentration by exposing a gas sample to an infrared light source and performing a physical measurement on the gas. For example, a non-dispersive infrared absorbance (NDIR) sensor measures the absorption of the infrared light a certain wavelengths and determines the gas concentration based on the amount of light absorption; and a photoacoustic sensor measures a change in pressure of the gas sample in the presence of infrared light and determines the gas concentration based on the change in pressure of the gas.

Photoacoustic sensors, which generally include an infrared light source and a microphone, are well-suited to low-cost and mass producible implementations because of their small size and their ability to be manufactured using common commercial semiconductor and packaging technologies. One issue with photoacoustic sensors, however, is their sensitivity to acoustic noise. Acoustic noise produced by machinery, traffic, or even human activity may interfere with the photoacoustic sensor's ability to perform acoustic measurements and degrade the accuracy of the sensor.

SUMMARY

In accordance with an embodiment, a method of measuring a gas concentration includes modulating an infrared light source according to a frequency-hopped sequence including time intervals, where the infrared light source is modulated at a first frequency during a first time interval, the infrared light source is modulated as at second frequency during a subsequent time interval, and the first frequency is different from the second frequency; receiving a microphone signal from an output of a microphone acoustically coupled to a gas exposed to infrared light produced by the infrared light source; bandpass filtering the microphone signal using a bandpass filter to produce a filtered microphone signal; adjusting a center frequency of the bandpass filter according to the frequency-hopped sequence, where the bandpass filter includes a first center frequency corresponding to the first frequency during the first time interval, the bandpass filter includes a second center frequency corresponding to the second frequency during the subsequent time interval, where the first center frequency is different from the second center frequency; and estimating the gas concentration from the filtered microphone signal.

According to another embodiment, a system for measuring a gas concentration includes an analysis circuit having a modulation output configured to be coupled to an input of an infrared light source, and bandpass filter having an input configured to be electrically coupled to an output of a microphone, where the analysis circuit is configured to modulate the infrared light source via the modulation output according to a frequency-hopped sequence including time intervals by modulating the infrared light source at a first frequency during a first time interval and at a second frequency different from the first frequency during a subsequent time interval, adjust a center frequency of the bandpass filter according to the frequency-hopped sequence, where the bandpass filter includes a first center frequency corresponding to the first frequency during the first time interval and a second center frequency different from the first center frequency, the second center frequency corresponding to the second frequency during the subsequent time interval, and estimate the gas concentration based on an output of the bandpass filter.

In accordance with a further embodiment, a method of measuring a gas concentration includes modulating an infrared light source according to a pulse sequence; receiving a microphone signal from an output of a microphone acoustically coupled to a gas exposed to infrared light produced by the infrared light source; multiplying the received microphone signal with a matched signal corresponding to the pulse sequence to form a despreaded microphone signal; bandpass filtering the despreaded microphone signal to form a bandpass filtered despreaded microphone signal; and estimating the gas concentration from the bandpass filtered despreaded microphone signal.

In accordance with another embodiment, A system for measuring a gas concentration includes an analysis circuit having a modulation output configured to be coupled to an input of an infrared light source, and a microphone input configured to be electrically coupled to an output of a microphone, where the analysis circuit is configured to modulate the infrared light source via the modulation output according to a pulse sequence; multiply a microphone signal received at the output of the microphone with a matched signal corresponding to the pulse sequence to form a despreaded microphone signal; bandpass filter the despreaded microphone signal to form a bandpass filtered despreaded microphone signal; and estimate the gas concentration from the bandpass filtered despreaded microphone signal.

BRIEF DESCRIPTION OF THE DRAWINGS

For a more complete understanding of the present invention, and the advantages thereof, reference is now made to the following descriptions taken in conjunction with the accompanying drawings, in which:

FIGS. 10A to 10E illustrate flow charts of embodiment photoacoustic calibration and estimation algorithms.

Figure 1A:
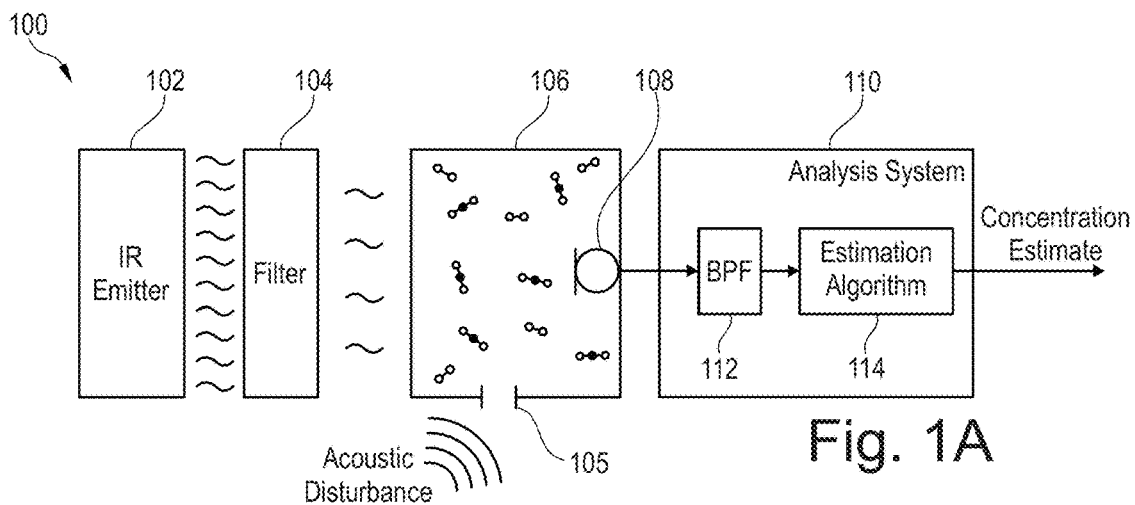
FIG. 1A illustrates an exemplary photoacoustic gas sensing system.

Corresponding numerals and symbols in different figures generally refer to corresponding parts unless otherwise indicated. The figures are drawn to clearly illustrate the relevant aspects of the preferred embodiments and are not necessarily drawn to scale. To more clearly illustrate certain embodiments, a letter indicating variations of the same structure, material, or process step may follow a figure number.

DETAILED DESCRIPTION OF ILLUSTRATIVE EMBODIMENTS

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The present invention will be described with respect to preferred embodiments in a specific context, a system and method for estimating a gas concentration using a photoacoustic sensor (PAS). Generally, a photoacoustic sensor includes an infrared (IR) light source that emits a time modulated IR emission, an optical filter and a detection volume with an integrated microphone that detects the photoacoustic pressure changes caused by the absorption of IR light taking place in the gas volume due to the presence of the measured gas, such as carbon dioxide. These measured pressure changes are used to estimate the concentration of the gas present. One advantageous aspect of photoacoustic gas sensors, especially microphone-based open non-resonant photoacoustic sensors, is the ability to implement such sensors inexpensively in very small form-factors, thereby making such sensors suitable for use in mobile and home applications. Such open non-resonant photoacoustic sensors include, for example, a microphone placed an a measurement volume, where the measurement system operates at relatively low frequencies, for example, less than 100 Hz. Microphone-based photoacoustic sensors, however, are sensitive to acoustic noise and interference. Accordingly, embodiments of the present invention are directed toward photoacoustic measurement systems that mitigate the effect of acoustic noise on photoacoustic measurements.

According to an embodiment, a concentration of a gas present in a sample is measured by performing a photoacoustic analysis of the sample. In various embodiments, this photoacoustic analysis is performed by exposing the gas sample to a pulsed infrared light source and measuring a pressure of the gas sample using a pressure sensor, such as a microphone. By modulating the pulsed infrared light source in a predetermined manner and processing the output of the pressure sensor according to the manner in which the pulsed infrared light source is modulated, the effect of acoustic noise and disturbance on the pressure measurement is attenuated.

For example, one embodiment system modulates the infrared light source according to a frequency-hopped sequence and filters the output of the pressure sensor with a bandpass filter having a center frequency corresponding to the frequency-hopped sequence. During operation, the system performs a series of gas concentration measurements at the various frequencies of the frequency-hopped sequence and applies a decision rule to the series of gas concentration measurements to remove outlier measurements and to identify frequencies at which acoustic noise is present. A final gas concentration measurement is determined based on the statistics of the series of gas concentration measurements after the outliers have been removed.

In another embodiment, the measurement system modulates the infrared light source according to a pulse sequence having a variable distance between pulses, multiplies the output of the pressure sensor with a matched signal function corresponding with the variable distance pulse sequence to form a despreaded signal, and determines a final gas concentration based on the despreaded signal. In such embodiments, spreading the received acoustic energy over a range of frequencies reduces the effect of acoustic noise. Advantages of embodiments include the ability to perform open non-resonant photoacoustic gas measurements in a noisy acoustic environment, thereby allowing for compact, inexpensive microphone-based gas measurement systems.

An advantage of embodiment photo acoustic sensors includes the ability to perform photoacoustic gas measurements with reduced sensitivity to acoustic noise and interference. Further advantageous aspects of some embodiments include the ability to reduce the effect of acoustic noise and interference without a priori knowledge of the position of the acoustic interferer. By spreading the frequency of the modulation provided to the infrared light source over a wide range of frequencies—either by frequency-hopping or by modulating the time between IR pulses, difficult to detect measurement biases and inaccuracies caused by acoustic interference completely overlapping the infrared emitter frequency can be mitigated.

FIG. 1A illustrates a block diagram of an exemplary open non-resonant photoacoustic sensor that includes infrared light source 102, optical filter 104, absorption chamber 106 including diffusion port 105 and microphone 108, and analysis system 110 that determines a gas concentration, such as carbon dioxide, within absorption chamber 106. In a conventional photoacoustic sensing system, infrared light source 102 transmits a train of pulses. Optical filter 104 allows infrared light associated with specific wavelengths associated with the specific gas being measured to reach absorption chamber 106. As infrared light source 102 turns on and off, the interior of absorption chamber 106 experiences a change of pressure associated with the modulated infrared light source 102. This change of pressure is detected by microphone 108, the output of which is analyzed by analysis system 110 to produce a gas concentration estimate. As shown, analysis system 110 includes bandpass filter 112 and analysis block 114 representing an estimation algorithm used to map measured microphone pressure to an estimated gas concentration.

In some circumstances, the change in pressure in absorption chamber 106 increases with increased gas concentration due to the gas absorbing energy from infrared light source 102. In addition to affecting the change in pressure, different gas concentrations may also affect the manner in which the pressure changes. For example, the slope and delay of the pressure change, as well as other transient characteristics of the pressure change may be affected by the concentration of the gas being measured. Thus, analysis block 114 may use a variety of measurement parameters including peak-to-peak pressure changes, the slope of the pressure change, and other parameters to determine the gas concentration estimate.

In conventional photoacoustic measurement systems, infrared light source 102 transmits the train of pulses at a fixed frequency. Thus, acoustic disturbances having frequency content that overlaps the fixed infrared transmission frequency may cause inaccuracies in the determined gas concentration estimate. An example of such inaccuracies are illustrated in FIGS. 1B and 1C that show waveform diagrams of gas concentration estimates in the presence of an acoustic interferers of different frequencies for a system in which infrared light source 102 is pulsed on and off at a frequency of 40 Hz and a 1000 ppm concentration of carbon dioxide is present within absorption chamber 106.

Figure 1B:
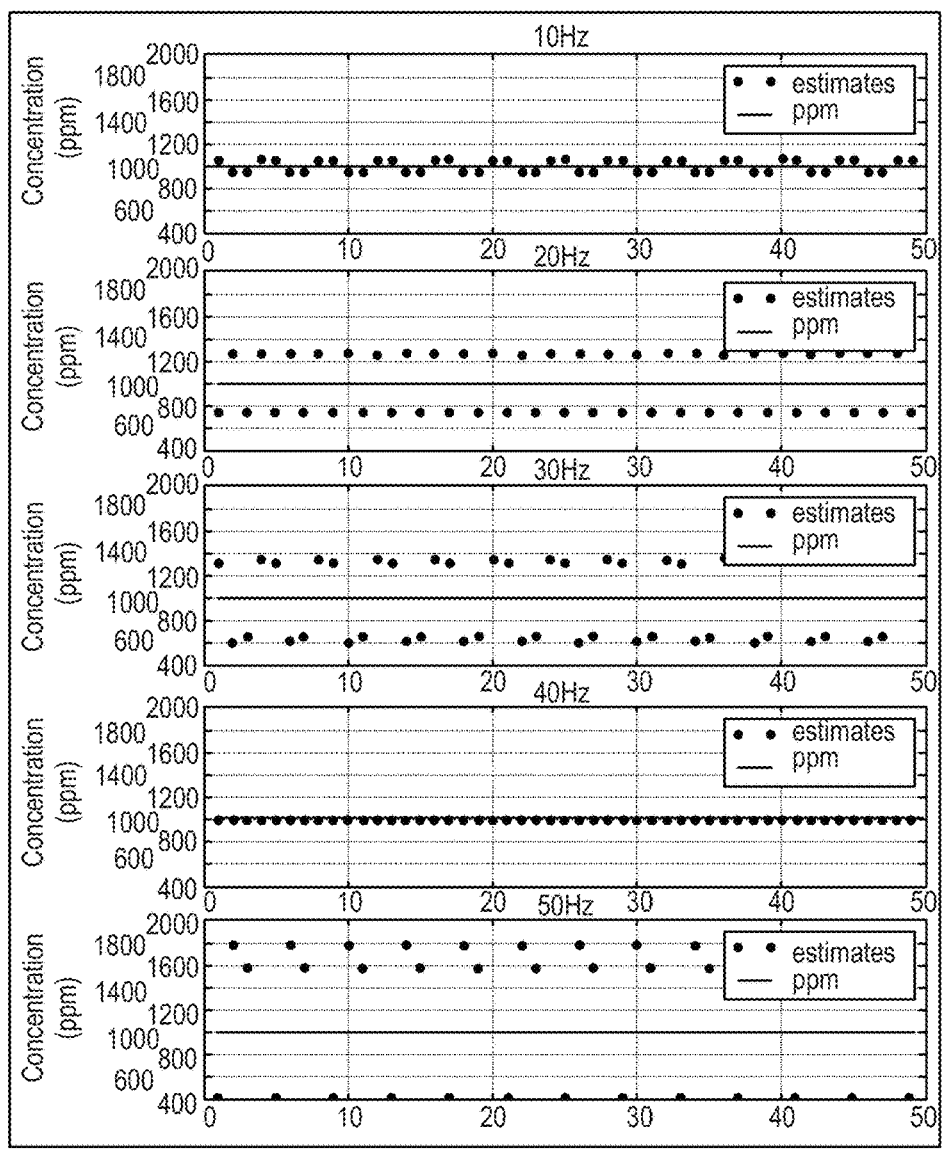
FIGS. 1B and 1C illustrate graphs showing the performance of a conventional photoacoustic gas sensing system.

FIG. 1B illustrates a set of graphs showing gas concentration estimates in the presence of a 90 dB SPL acoustic interference that corresponds to a 10 mV signal at the output of microphone 108 for frequencies of 10 Hz, 20 Hz, 30 Hz, 40 Hz and 50 Hz. With a 10 Hz, disturber, the measurement error is about 5% since the disturbing frequency is attenuated by the stopband or transition band of passband of bandpass filter 112. The measurement errors for 20 Hz, 30 Hz and 50 Hz disturbers are significantly more severe at 25%, 40% and 80%, respectively. The increase in measurement error for higher frequencies is partially due to the high-pass response of microphone 108, which provides attenuation for frequencies lower than the frequency at which infrared light source 102 is modulated. For example, in some embodiments, the microphone has a lower cutoff frequency of between about 20 Hz and about 30 Hz. However, the lower cutoff frequency may be different in other embodiments. The increase in measurement error for higher frequencies is partially due to the high-pass response of microphone 108, which provides attenuation for frequencies lower than the frequency at which infrared light source 102 is modulated. The error for the 40 Hz appears low because the disturber is introduced in phase with the infrared pulses. In situations where the disturber is out of phase with the infrared pulses, the measurement errors would be significantly higher.

Figure 1C:
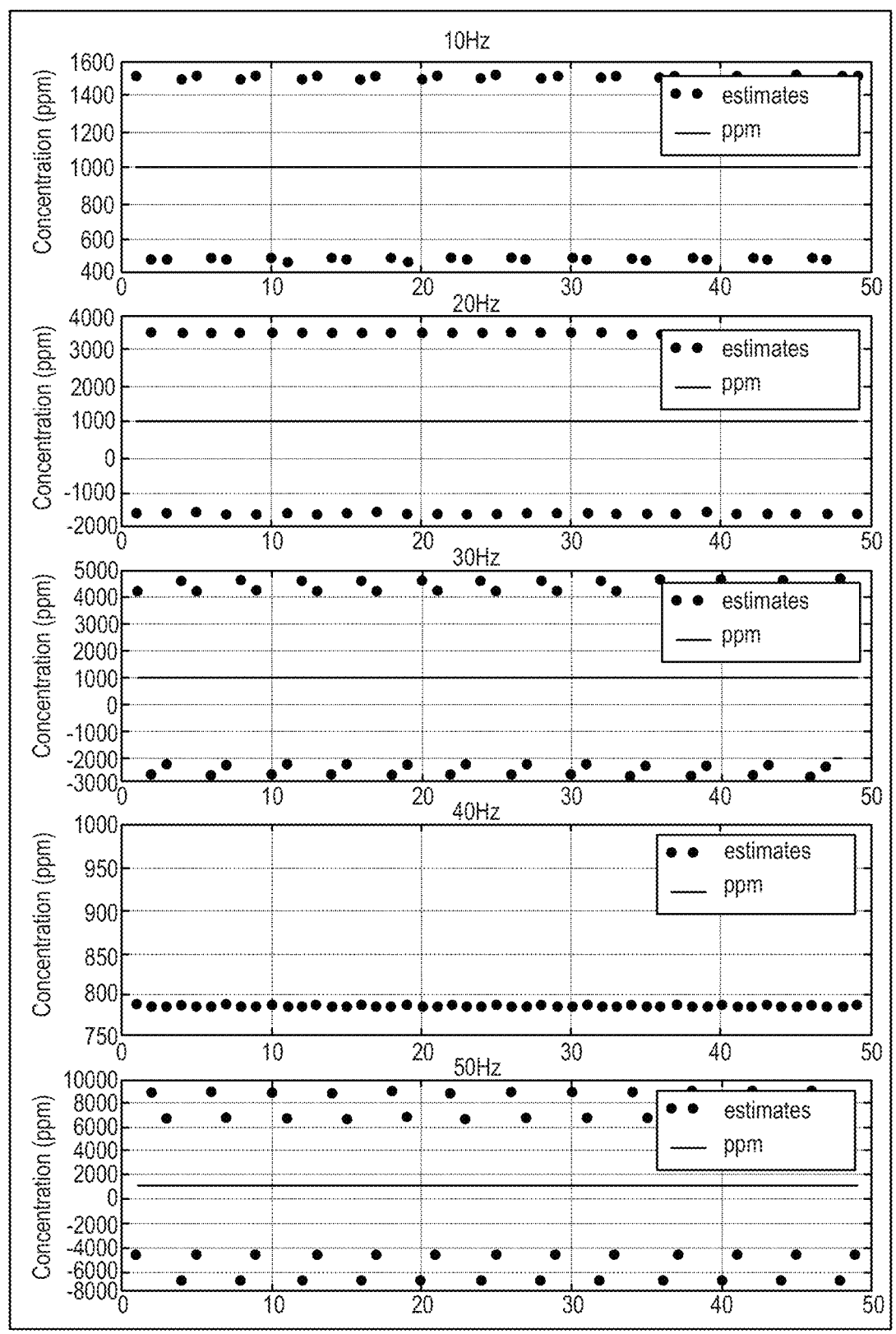

FIG. 1C illustrates a set of graphs showing gas concentration estimates in the presence of a 110 dB SPL acoustic interference that corresponds to a 100 mV signal at the output of microphone 108 for frequencies of 10 Hz, 20 Hz, 30 Hz, 40 Hz and 50 Hz. With a 10 Hz, disturber, the measurement error is about 5% since the disturbing frequency is attenuated by the stopband or transition band of passband of bandpass filter 112. The measurement errors for the 10 Hz, 20 Hz, 30 Hz, 40 Hz and 50 Hz disturbers are 50%, 350%, 400%, 20% and 900%, respectively.

Figure 2A:
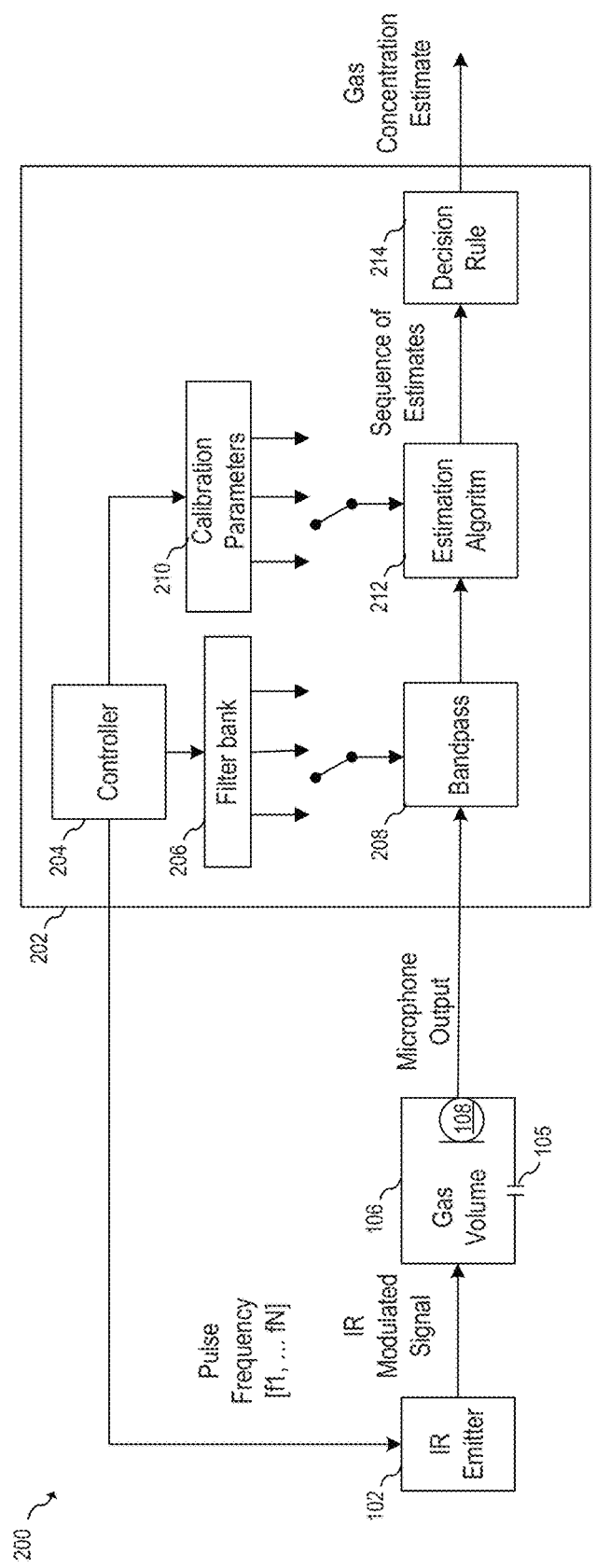
FIG. 2A illustrates a block diagram of an embodiment frequency-hopped photoacoustic gas sensing system.

FIG. 2A illustrates a photoacoustic measurement system 200 according to an embodiment of the present invention in which infrared light source 102 is frequency modulated using a frequency hopping sequence instead of being modulated at a fixed frequency. The modulating signal includes a succession of N different frequencies fi in [f1 . . . fN]. In some embodiments, each single frequency can be repeated Np times to ensure a certain redundancy. The set of frequencies may be selected in an appropriate range to provide good performance and reduce complexity.

In various embodiments, the choice of the frequencies in the sequence may be selected to account for a variety of aspects. For example, the frequencies may be chosen to correspond with a frequency range that is supported by the particular microphone technology being used. In the embodiments described herein, a frequency range of between 20 Hz and 90 Hz corresponds to the particular MEMS microphone technology being used. In such embodiments, frequencies greater than about 40 Hz have increased signal to noise ratios compared with the lower frequencies. In some embodiments, the frequencies [f1 . . . fN] may be chosen to be very close to each other such that the difference between each adjacent frequency is between about 2 Hz and about 5 Hz. In such embodiments, a single bandpass filter response for bandpass filter 208 and/or a single set of calibration parameters 210 for estimation algorithm 212 could be used by a post processing system in order to reduce system complexity and the amount of memory needed to implement the system. In some embodiments, the single bandpass filter response may be shifted to adapt to the particular frequency [f1 . . . fN] being used to modulate infrared light source 102. In embodiments in which frequencies [f1 . . . fN] are spaced farther apart, for example, where each adjacent frequency is about 20 Hz away from each other, a bandpass filter 208 may be designed to have a wider bandwidth and less performance restraints. In addition, the selection of frequencies [f1 . . . fN] may be based on a priori knowledge of the nature of the narrowband interferer. For example, in systems in which an interferer is known to exist as a particular fixed frequency, the corresponding interference frequency may be omitted from the set of frequencies [f1 . . . fN]. It should be understood, however, that different measurement system implementations and/or other microphone technologies may result in different frequency ranges than those specifically described herein.

As shown, photoacoustic measurement system 200 includes infrared light source 102, absorption chamber 106 including diffusion port 105 and microphone 108, and analysis system 202. In some embodiments, an optical filter may be disposed between infrared light source 102 and absorption chamber 106. In addition to determining a gas concentration estimate based on the output of microphone 108, analysis system 202 also provides a frequency modulated signal to infrared light source 102.

As shown, analysis system 202 includes an adjustable bandpass filter 208 that filters the microphone signal using a transfer function based on pulse frequency provided to infrared light source 103; estimation algorithm block 212 that determines a series of estimated gas concentrations based on the filtered microphone signal; and a decision rule block 214 that selects estimates from the series of estimates determined by estimation algorithm block 212 in order to provide a more accurate gas concentration estimate. Controller 204 represents a control function of analysis system 202 and coordinates the modulation of infrared light source 102 with the operation of bandpass filter 208, estimation algorithm 212 and decision rule block 214. Filter bank 206 provides filter coefficients to bandpass filter 208, and calibration parameter block 210 provides calibration parameters to estimation algorithm block 212.

Infrared light source 102 may be implemented, for example, using infrared light sources known in the art. In some embodiments, infrared light source 102 is implemented using a MEMS heater circuit having a low thermal mass. In one embodiment, infrared light source reaches a temperature of between 300° C. and 800° C. when activated. In alternative embodiments, other infrared light source structures may be used.

In some embodiments, microphone 108 is implemented using a MEMS microphone having a generally constant gain and sensitivity over its operation range (e.g., between about 30 Hz and about 100 Hz). However, microphone gain differences over frequency may be compensated by the system. In alternative embodiments, other microphone or pressure sensor structures known in the art may also be used.

Analysis system 202 may be implemented in a number of different ways. From a physical standpoint, analysis system 202 may be implemented on a single integrated circuit or using a plurality of integrated circuit components. From an architectural standpoint, each of the blocks shown in analysis system 202 may be implemented using dedicated circuit components, such as logic circuits, for each function. Alternatively, some or all of the blocks shown in analysis system 202 may be implemented using a processor that executes code that defines the function of each block. In some embodiments, mathematically intensive blocks such as bandpass filter 208, estimation algorithm block 212 and/or decision rule block 214 may be implemented using a digital signal processor (DSP) core.

Figure 2B:
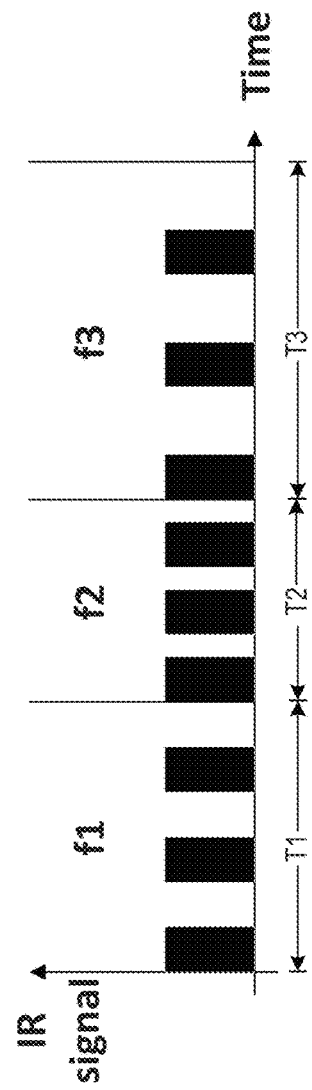
FIG. 2B illustrates a timing diagram of frequency sequence used to modulate an infrared light source of the embodiment photoacoustic gas sensing system of FIG. 2A.

During operation, controller 204 provides infrared light source 102 with a frequency modulated pulse train, such as that illustrated in FIG. 2B. As shown, the modulating frequency is f1 during time interval T1, f2 during time interval T2, and f3 during time interval T3. The length of each time interval T1, T2 and T3 may be the same or different from each other. During each time interval, the transfer function of bandpass filter 208 is modified according to the frequency of the modulation applied to infrared light source 102. In some embodiments, the center frequency of bandpass filter 208 is adjusted to be close to or equal to frequency at which infrared light source 102 is modulated. For example, during time interval T1, bandpass filter 208 is configured to have a center frequency of f1, during time interval T2, bandpass filter 208 is configured to have a center frequency of f2, and during time interval T3, bandpass filter 208 is configured to have a center frequency of f3. Alternatively other center frequencies may be selected. In some embodiments, the difference between the modulation frequency and the center frequency of bandpass filter is within 2 Hz for systems in which the selected modulation frequencies are spaced closely together. In alternative embodiments this tolerance may be different depending on the frequency plan and the bandwidth of the bandpass filter 208. It should be understood that the example frequency modulation scheme shown in FIG. 2B is just one of many possible embodiment frequency modulation schemes. Any number of frequencies two or greater can be used to implement embodiment frequency-hopped modulation schemes. In some embodiments, frequencies are chosen to be in a frequency range in which the photoacoustic signal is maximized, for example, between 30 Hz and 100 Hz. In one specific example, the frequencies are chosen to be 36 Hz, 40 Hz and 44 Hz, however, other frequencies could be chosen.

Bandpass filter 208 may be implemented using different filter structures known in the art. For example, in digital implementations, bandpass filter 208 may be implemented in the time domain using an infinite impulse response (IIR) filter or a finite impulse response (FIR) filter. In other embodiments, bandpass filtering is implemented the frequency domain using FFTs and element-wise multiplication (correlation) of obtained frequency vectors, as is further described below with respect to FIGS. 3A and 3B. In various embodiments, filter coefficient sets corresponding to the various modulation frequencies are stored in filter bank 206 and/or in memory and loaded into bandpass filter 208 during each frequency modulation time interval. In some embodiments, the filter function of bandpass filter 208 is a matched filter function that is matched to the expected incoming signal.

Figure 3A:
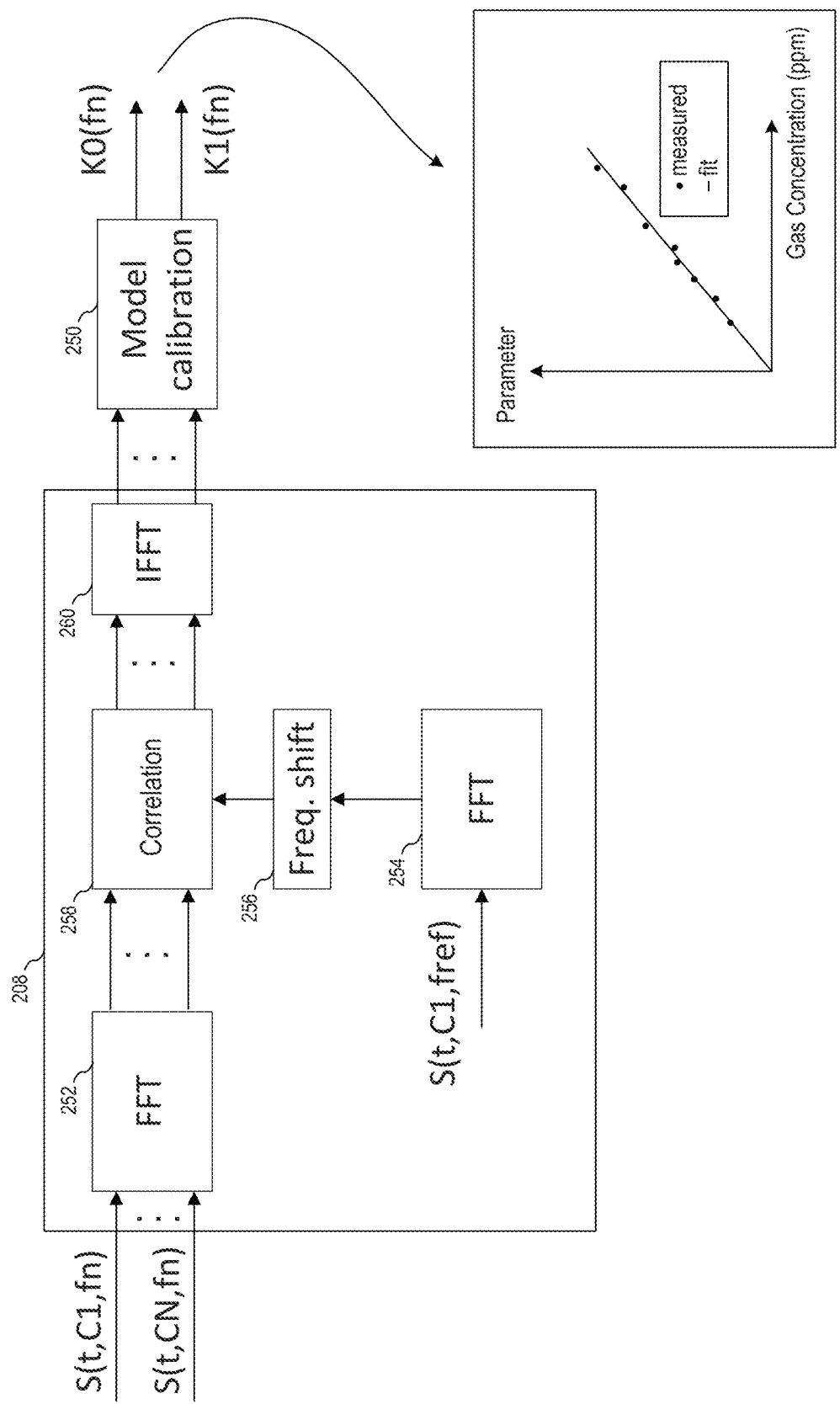
FIGS. 3A and 3B illustrate block diagrams showing the operation of an embodiment frequency-hopped photoacoustic gas sensing system during calibration and normal operation.

FIG. 3A illustrates an implementation of bandpass filter 208 shown in the context of performing an estimation model calibration. As shown, bandpass filter 208 is implemented using FFT blocks 252 and 254, correlation block 258, frequency shift block 256 and inverse FFT (IFFT) block 260. During operation, FFT block 252 performs a fast-Fourier transform of incoming microphone signal $S(t,C1,fn)$ and reference impulse response $S(t,C1,fref)$. Frequency shift block 256 shifts FFT of the impulse response to correspond with the desired center frequency of bandpass filter 208. Correlation block 258 multiplies the outputs of FFT block 252 and frequency shift block 256 an element by element basis, and IFFT block 260 transforms the frequency domain output of correlation block 258 back into the time domain. It should be understood that the implementation of bandpass filter 208 shown in FIG. 3A is just one of many examples of how bandpass filter 208 could be implemented. In alternative embodiments, the filtering operation of bandpass filter 208 may be implemented by performing a convolution in the time domain. In such embodiments, a different reference impulse (in the form of FIR coefficients), would be used for each programmable transfer function.

During calibration, a series of gas concentration measurements are made over a space of different gas concentrations [C1 . . . CN] and different infrared light source modulation frequencies [f1 . . . fn]. In an embodiment, reference impulse response $S(t,C1,fref)$ is derived by performing a reference concentration measurement at a reference frequency fref. In some embodiments, the reference concentration is a low or zero gas concentration and the reference frequency is a lowest frequency used by the system. For example, in an implementation that uses, 36 Hz, 40 Hz and 44 Hz, the reference frequency is 36 Hz. Alternatively, other reference frequencies could be used.

During calibration, model calibration block 250 analyzes and parameterizes the output of bandpass filter 208 and builds a linear fit model, as represented by K-coefficients $K0(fn)$ and $K1(fn)$ for each modulation frequency, as is explained below. Parameters that may be used by model calibration block 250 and estimation algorithm 212 may include a slope of a rising pulse, the area under the pulse, a phase of the signal, and/or other parameters described below.

Figure 3B:
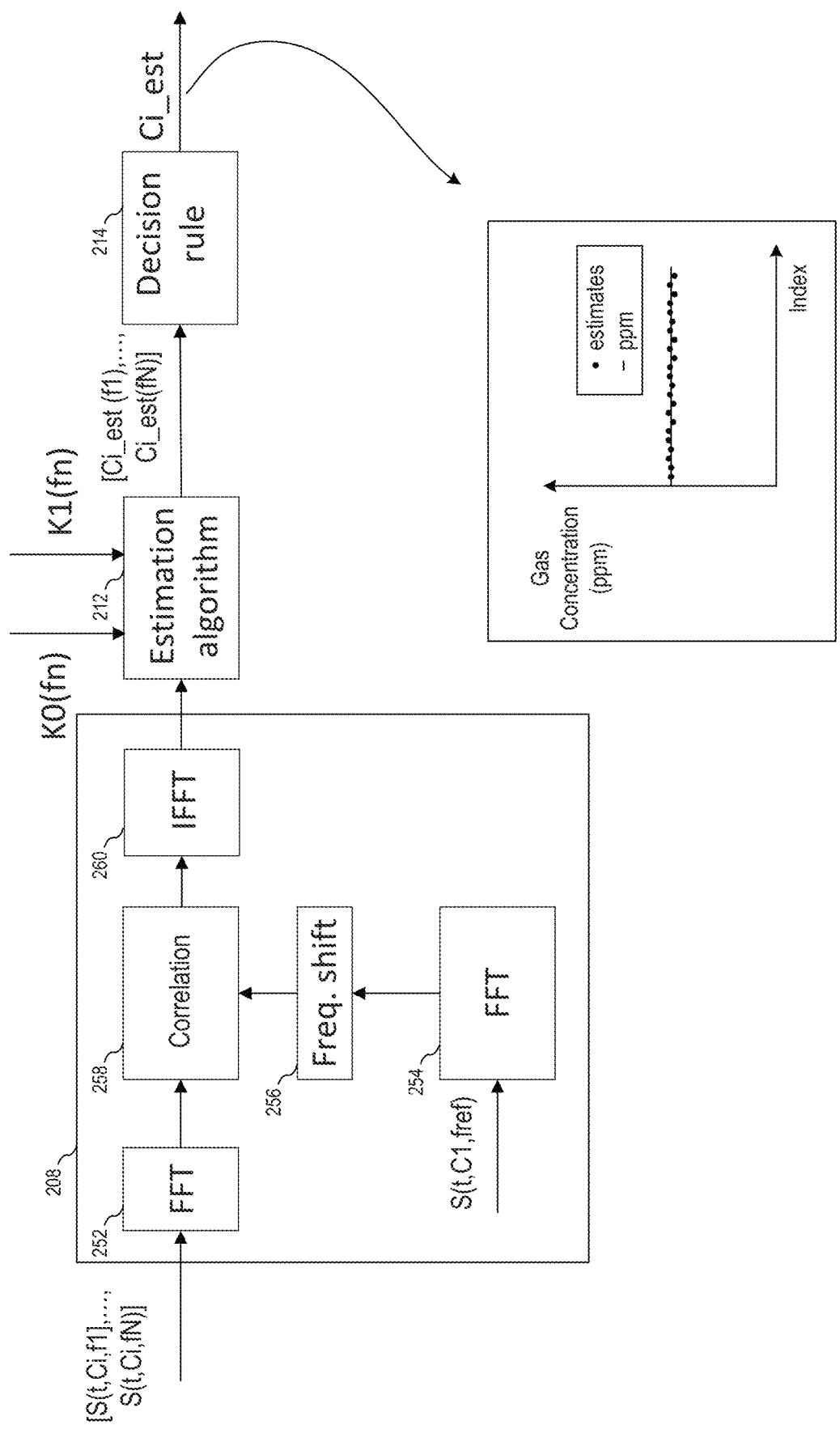

After the calibration is performed, K-coefficients $K0(fn)$ and $K1(fn)$ are applied to estimation algorithm 312 as shown in FIG. 3B. During each time interval, bandpass filter 208 filters the microphone signal $[S(t,Ci,f1), \ldots, S(t,Ci,fN)]$, which is a function of unknown gas concentration Ci and modulation frequency fn. Estimation algorithm 212 analyzes and parameterizes the output of bandpass filter 208 and uses a linear fit model represented by K-coefficients $K0(fn)$ and K1(fn) to determine a gas concentration estimate [Ci_est (f1), ... , Ci_est(fN)] for each frequency [f1 ... fn]. Decision rule block 214 removes outlier gas concentration measurements, and determines gas concentration measurement Ci_est based on the remaining estimates. In some embodiments, decision rule block 214 implements a majority rule that selects concentration estimates that recur more often in the vector of estimates.

In one embodiment, an outlier removal algorithm is described as follows. An FH-signal is considered where $M_i$ pulses are transmitted for each frequency $f_i$, with i=[1, 2, ... , $N_f$]. A generic estimate $C_{est}^{n_i}(f_i)$ is obtained through a generic algorithm for the $n_i$-th pulse corresponding to frequency $f_i$ to obtain the following sequence of estimates:

$$\left[ C_{est}^1(f_1), \ldots , C_{est}^{M_1}(f_1), \ldots , C_{est}^{n_j}(f_j), \ldots ,\right. \quad (1)$$
$$\left. C_{est}^1(f_{N_f}), \ldots , C_{est}^{M_{N_f}}(f_{N_f}) \right]$$

Assuming that an interferer is affects frequency $f_j$ in the sequence, the corresponding estimates $C_{est}^{n_j}(f_j)$ for all $n_j \in M_j$ pulses may be inaccurate and thus be candidates for elimination. To this end, an embodiment approach to eliminating outliers is as follows:

1) Obtain the average estimate for each group of pulses:

$$C_{ave}(f_i) = \frac{\sum_{n_i=1}^{M_i} C_{est}^{n_i}(f_i)}{M_i}. \quad (2)$$

2) Compute the Euclidian distance between each of the average estimates:

$$E_{ave}^{i,j} = \sqrt{|C_{ave}(f_i) - C_{ave}(f_j)|^2}. \quad (3)$$

3) Eliminate the group of estimates corresponding to the average estimate with the largest Euclidean distance from all the other groups. For example, for the special case of $N_f=3$ and an interferer at $f_j=2$:

$$(E_{ave}^{1,3} + E_{ave}^{1,2}) \approx (E_{ave}^{3,1} + E_{ave}^{3,2}) \ll (E_{ave}^{2,3} + E_{ave}^{2,1}). \quad (4)$$

and $C_{est}^{n_2}(f_2)$ for $n_2 \in M_2$ are the estimates to be eliminated.

4) Base the final estimate on the average of the remaining groups. For the special case above:

$$C_{est}^{final} = \frac{C_{ave}(f_1) + C_{ave}(f_3)}{2}. \quad (5)$$

It should be understood that the outlier removal algorithm described above it just one of many possible outlier removal algorithms that may be applied to embodiment photoacoustic gas sensing systems. In alternative embodiments, other algorithms known in the art may be used.

Figure 4A:
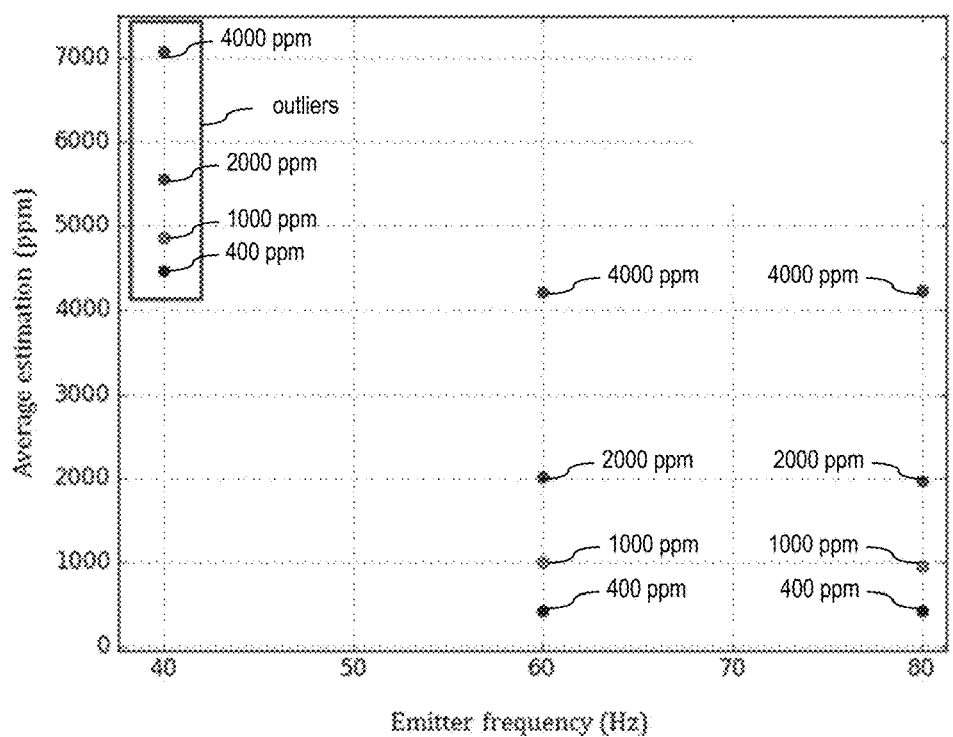
FIGS. 4A and 4B illustrate graphs showing the performance of an embodiment frequency-hopped photoacoustic gas sensing system.
Figure 4B:
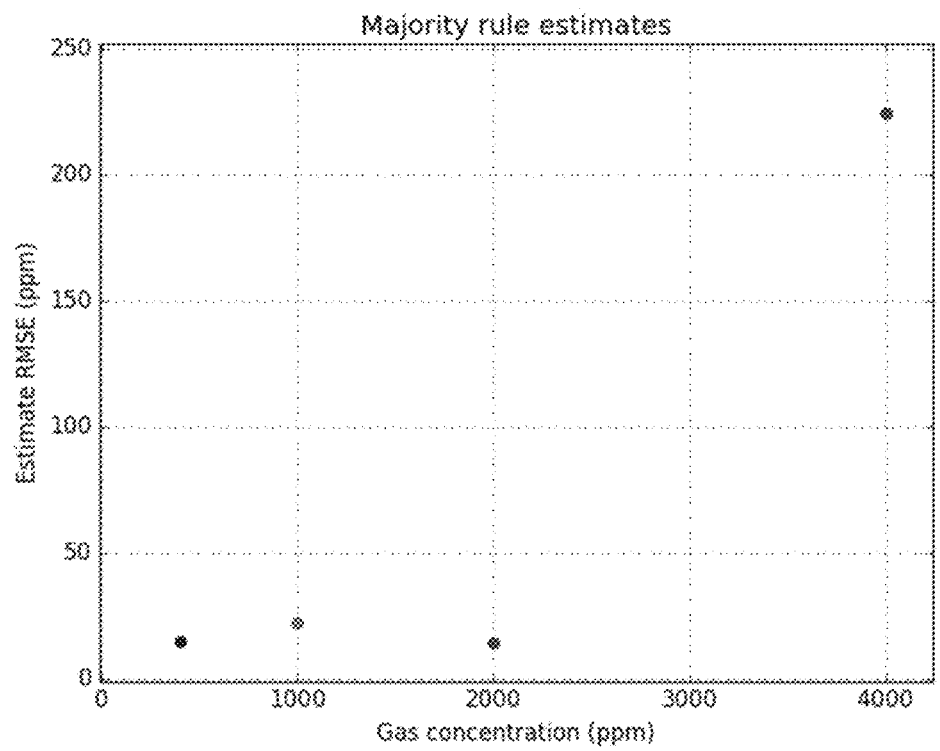

FIGS. 4A and 4B illustrate graphs that show the performance of an embodiment photoacoustic system that utilizes frequency hopping. FIG. 4A illustrates a graph of estimated gas concentration vs. infrared light source modulation frequency for gas concentrations of 400 ppm, 1000 ppm, 2000 ppm and 4000 ppm and frequencies of 40 Hz, 60 Hz and 80 Hz, respectively, in the presence of a 90 dB SPL interferer having a frequency of 40 Hz. As shown, the estimates made for the 60 Hz and 80 Hz frequencies have values that more closely correspond to the estimated gas concentration, while the measurements made with the 40 Hz modulation frequency (which is the same as the interference frequency) show significantly elevated gas concentrations. In embodiments of the present invention, decision rule block 214 would remove the 40 Hz measurement and average the remaining measurements made at 60 Hz and 80 Hz to produce a more accurate final gas concentration estimate. The root mean square error RMSE of these majority estimates for each gas concentration is graphed in FIG. 4B. It should be understood that the performance of the photoacoustic gas measurement system illustrated in FIGS. 4A and 4B represents the performance of one specific system implementation. Other systems may perform differently depending on its particular implementation and operating environment.

Figure 5:
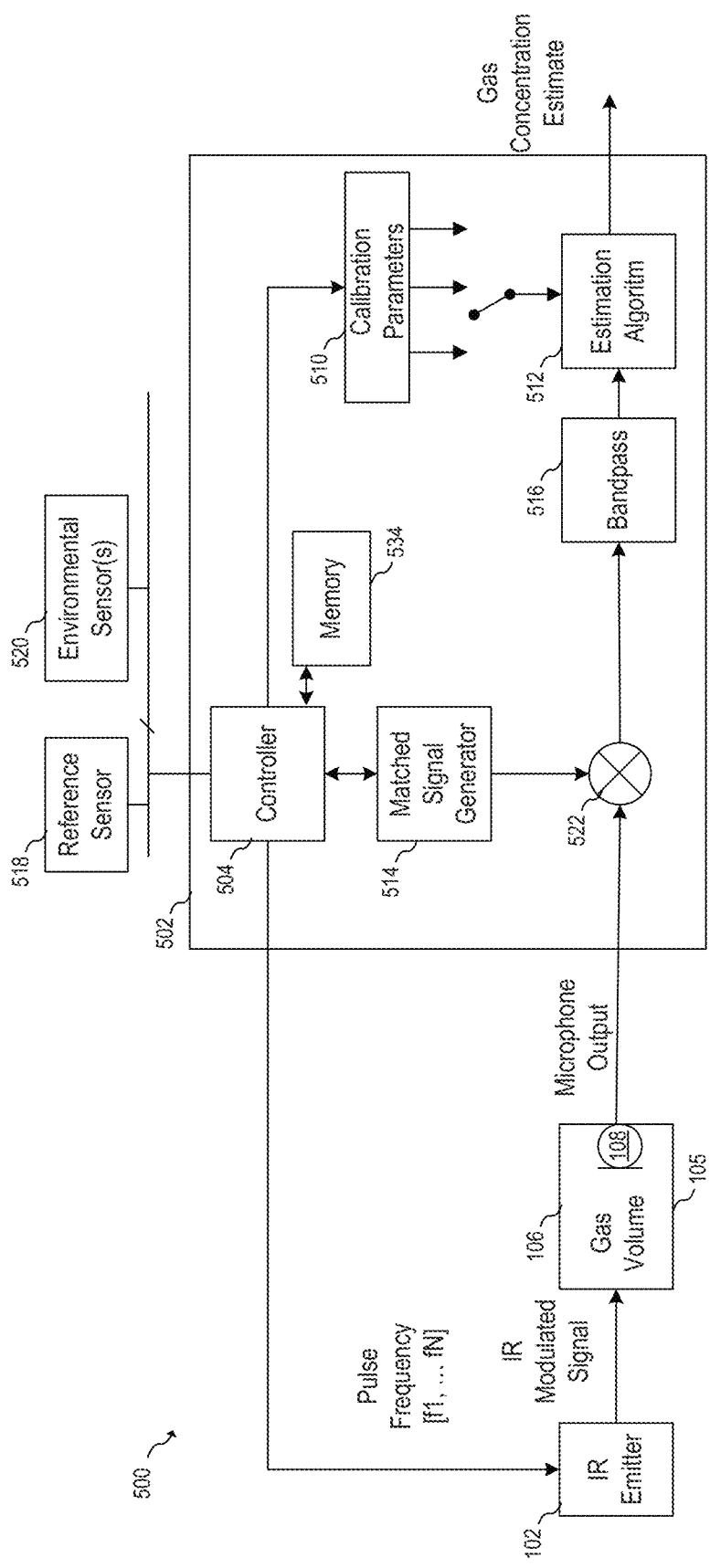
FIG. 5 illustrates a block diagram of an embodiment matched-signal photoacoustic gas sensing system.

FIG. 5 illustrates a photoacoustic measurement system 200 according to an embodiment of the present invention in which a pulse sequence having a variable time between pulses modulates infrared light source 102. The time between pulses is varied so as to give the microphone signal a characteristic signature that differentiates the gas measurement from a potential interferer. Varying the time between pulses also spreads the energy of the microphone signal over frequency. The received microphone signal is multiplied ('de-spreaded') with a known periodic signal matched to the microphone output in ideal conditions (no interference) and in the absence of gas. In various embodiments, this procedure enhances the signal to interference ratio of the microphone signal, thereby allowing for interference suppression prior to the estimation of the gas concentration. An estimation metric based on the obtained signal is extracted and fed to a generic calibration and estimation algorithm, such as a linear fit regression.

As shown, photoacoustic measurement system 500 includes infrared light source 102, absorption chamber 106 including diffusion port 105 and microphone 108, and analysis system 502. In some embodiments, an optical filter may be placed between infrared light source 102 and absorption chamber 106. In addition to determining a gas concentration estimate based on the output of microphone 108, analysis system 502 also provides a pulse modulated signal to infrared light source 102.

As shown, analysis system 202 includes a matched signal generator 514 that generates a pulse modulated sequence used to modulate infrared light source 102. A matched-signal based on the pulse modulated sequence is multiplied with the microphone output signal via multiplier 522. Thus, the pulse modulated sequence, or parameters related to the pulse modulated sequence may be stored in memory 534. Bandpass filter 516 filters the multiplied signal to remove noise and interference, and estimation algorithm block 512 determines a series of estimated gas concentrations based on output of bandpass filter 516. Controller 504 represents a control function of analysis system 502 and coordinates the modulation of infrared light source 102 with the operation of estimation algorithm 512. In some embodiments, the output of reference sensor 518 and environmental sensor(s) 520, which may include temperature, humidity and pressure sensors, are used to adjust baseline or calibration parameters 510.

In an embodiment, the time distance between pulses used to modulate infrared light source 102 is varied to obtain a signal of the type:

$$p(t) = \Sigma_{n=1}^t p(t - \tau_{mod(n, N_p)}). \quad (6)$$

In other terms, pulses from infrared light source 102 have a variable distance according to a known sequence of $\{\tau_i\}_{i=1, \ldots, N_p}$ of period $N_p$. The particular sequence used may be selected, for example, to increase or maximize the separability of the signal at the output of microphone 108 from the interferer. Such a sequence may be chosen to give the resulting signal a characteristic signature. The longer and less repeatable a sequence is, the greater the separability between the measured signal and the measured acoustic interference. A particular sequence may also be chosen to increase or maximize the separability of different concentration values for the estimation algorithm. Here, sequences with a lower noise floor and lower ripple have greater separability for different concentration values.

A special case of the modulation described above is a signal where the original sequence of pulses at fixed distance ($1/F_{IR}$, with $F_{IR}$=40 Hz) is amplitude modulated with a known and periodic sequence of '1's and '0''s, where a '0' corresponds to skipping a pulse. This can be seen as the signal in the above equation for p(t) where the $\{\tau_i\}_{i=1, \ldots, N_p}$ are multiples of $1/F_{IR}$.

In an embodiment, the output of microphone 108 is first multiplied with a 'matched' signal via multiplier 522. This corresponds to a signal received in ideal conditions (e.g., no interference/noise and in the absence of gas), which has been obtained and stored in the calibration phase or provided by a reference sensor. The signal is then filtered with bandpass filter 516, the gas concentration is estimated using a calibrated estimation algorithm (e.g., a linear fit regression), and a final gas concentration estimate is produced.

Figure 6A:
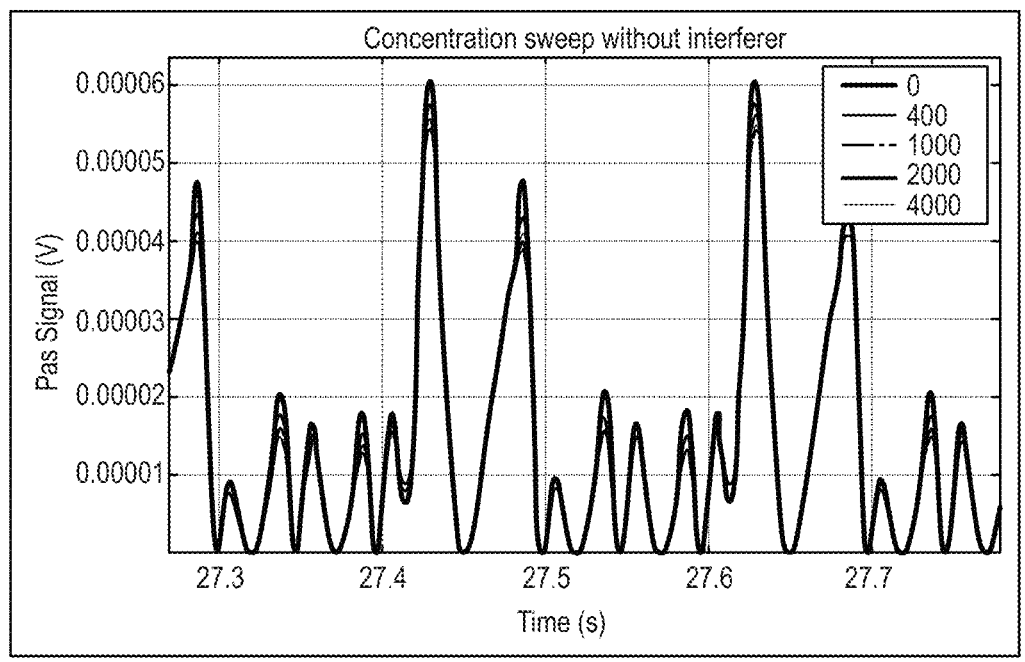
FIGS. 6A to 6C illustrate waveform diagrams associated with matched-signal sequences for an embodiment matched-signal photoacoustic gas sensing system.
Figure 6B:
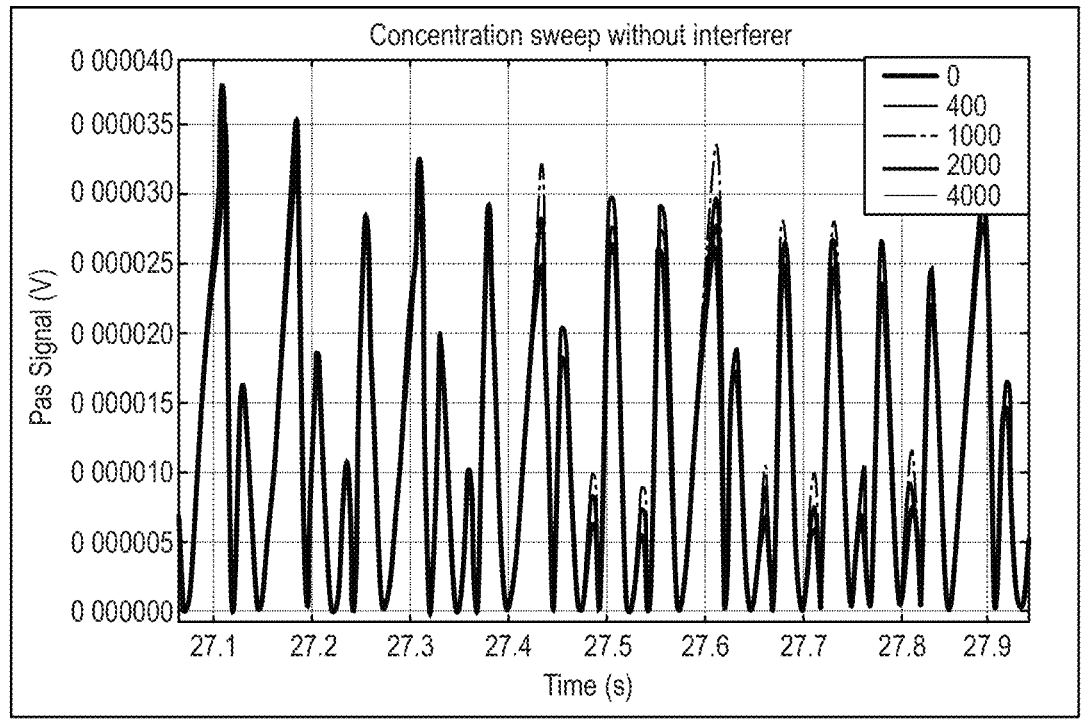
Figure 6C:
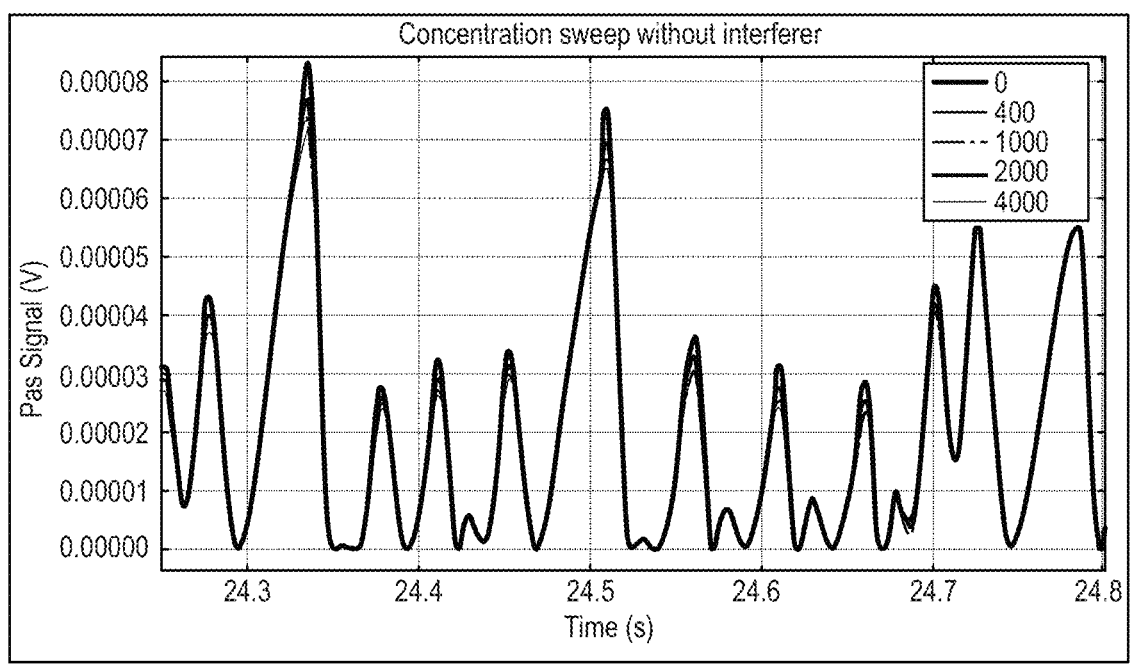

In one specific example, the signal is amplitude modulated by a known periodic Np-long sequence of 0's and 1's (e.g. [1 1 0 0 1 0 1 0]) to obtain an output (in the absence of noise/interference) such as the output illustrated in FIG. 6A that shows the output of microphone 108 over time measuring different gas concentrations for the sequence [1 1 0 0 1 0 1 0]. Note that longer sequences are possible as shown in FIG. 6B, which illustrates the output of microphone 108 over time while measuring different gas concentrations for the sequence [1 0 0 1 0 1 0 0 1 0 1 0 0 1 0 1 0 1 0 0 1 0 1 0 1 0 1 0 0]. In some cases, sequences with a long series of consecutive 1's or 0's may create elevated noise floors or small ripples as shown in FIG. 6C.

Figure 7:
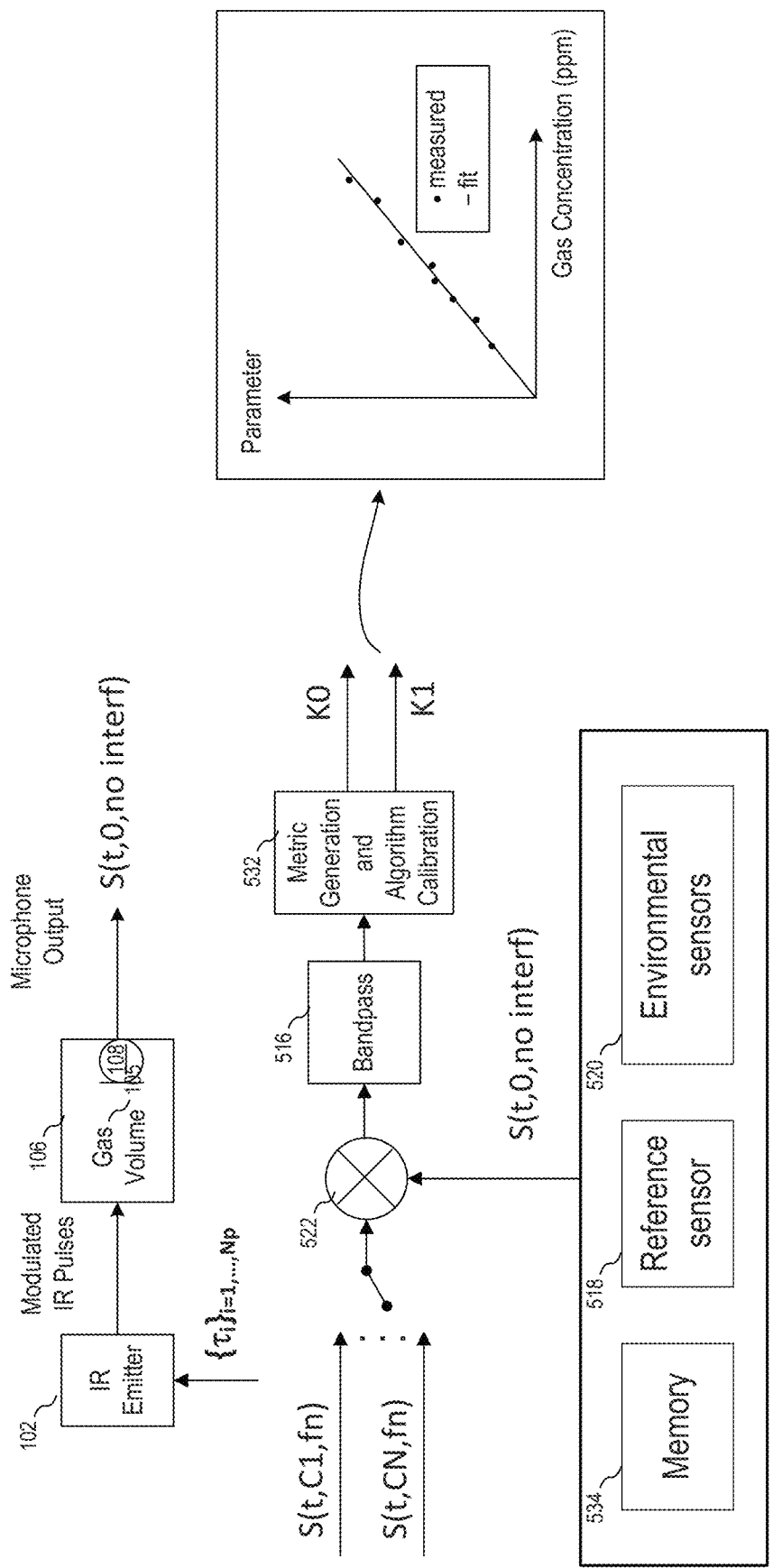
FIG. 7 illustrates a block diagram showing the operation of an embodiment matched signal photoacoustic gas sensing system during calibration.

FIG. 7 illustrates a block diagram of an embodiment calibration system configuration. During calibration, a reference sequence S(t,0,no interf) is derived by performing a preliminary calibration measurement at a zero (or minimal) gas concentration in a quiet environment while modulating infrared light source 102 with a predetermined matched sequence. This reference sequence may be stored, for example, in memory 534. Next, a series of gas concentration measurements [S(t,C1,fn) . . . S(t,CN,fn)] are made over a space of different gas concentrations [C1 . . . CN], which are multiplied by the reference sequence using multiplier 522. The multiplied output is bandpass filtered. Metric generation and algorithm calibration block 532 then analyzes and parameterizes the output of bandpass filter 208 and builds a linear fit model represented by K-coefficients K0 and K1. This linear fit model maps the measured metrics and parameters into a ppm concentration. Parameters that may be used by metric generation and algorithm calibration block 532 include, for example, a slope of a rising pulse, the area under the pulse, a phase of the signal, and/or other parameters described below. In some embodiments, measurements, such as temperature, humidity and pressure made by environmental sensors 520 may be used by metric generation and algorithm calibration block 532 during calibration, for example, to adjust baseline values.

In some embodiments, this preliminary calibration may be performed using reference sensor 518. This reference sensor 518 may be a sensor that is constructed in a similar manner as microphone 108, but is configured in a manner that it does not react to a specific gas. In some embodiments, reference measurements made by reference sensor 518 may be used to perform differential measurements in conjunction with the measurements made by microphone 108. In such embodiments, changing environmental parameters such as temperature and pressure, are common to both microphone 108 and reference sensor 518. As such, these common mode sources of error can be removed by performing differential measurements.

During normal operation, the output of microphone 108 is multiplied by the waveform stored in memory 534. This has the effect of recovering the original signal while spreading the narrowband 'in-band' interferer. The subsequent bandpass filtering operation performed by bandpass filter 516 suppresses out-band interferers.

Figure 8A:
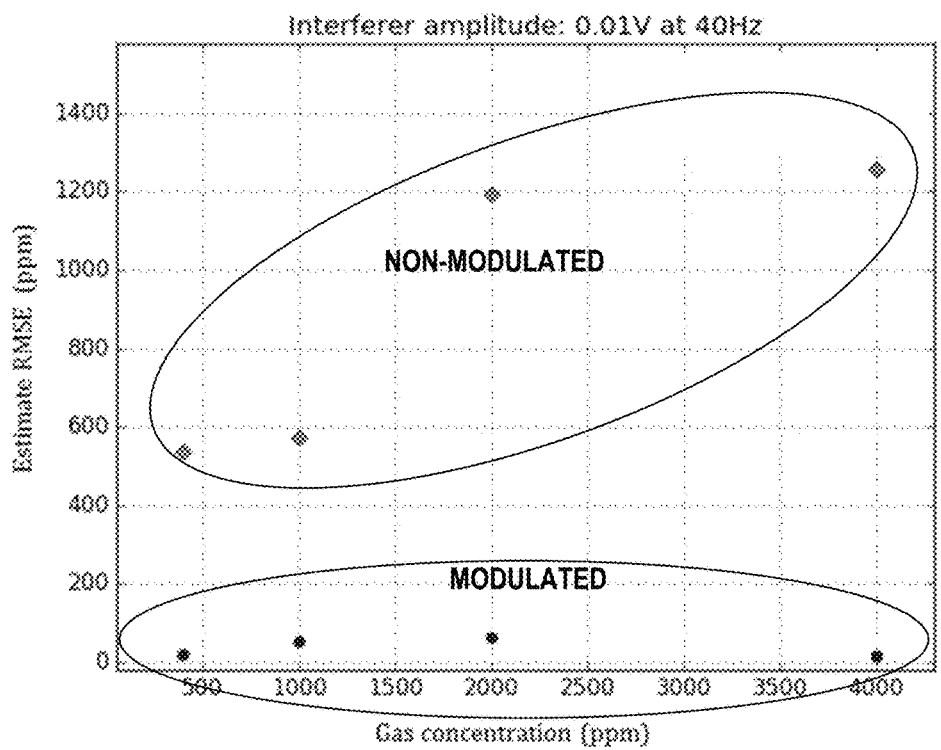
FIG. 8A to 8C illustrate graphs showing the performance of an embodiment matched-signal photoacoustic gas sensing system.
Figure 8B:
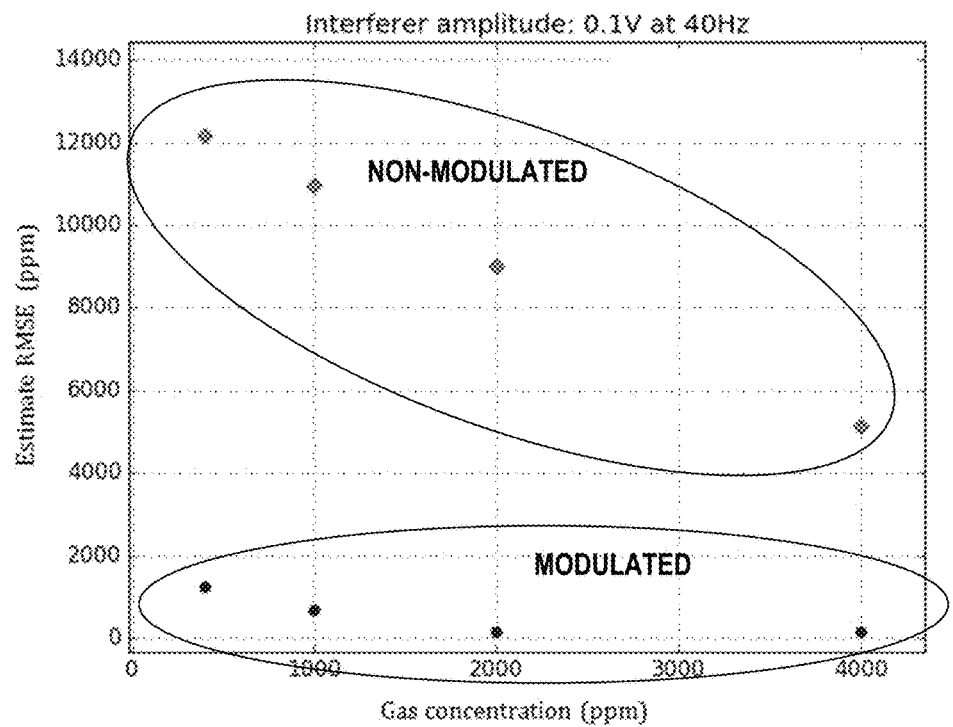
Figure 8C:
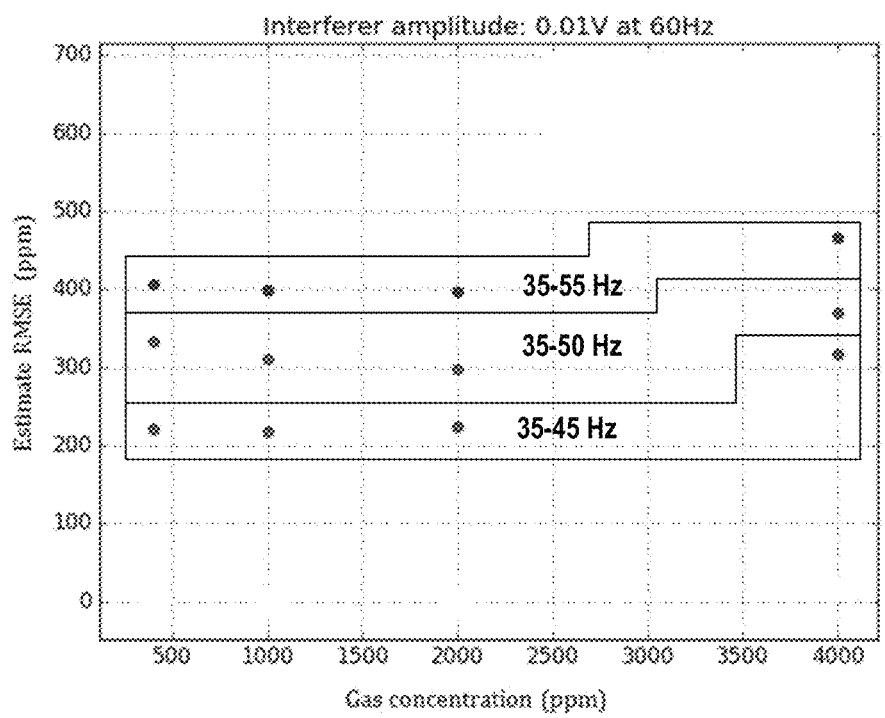

FIGS. 8A-8C illustrate graphs that show the performance of an embodiment photoacoustic system that utilizes embodiment matched sequence methods. FIG. 8A illustrates a graph of the estimated root mean square error RMSE vs estimated gas concentration for gas concentrations of 400 ppm, 1000 ppm, 2000 ppm and 4000 ppm in the presence of a 90 dB SPL 40 Hz interferer for an embodiment system that utilizes embodiment matched-filter techniques (MODULATED) and for a system that does not utilize embodiment matched filter techniques (NON-MODULATED). As can be seen, the estimated RMSE is significantly less than 100 ppm for all measurements made by the system that utilizes embodiment matched filter techniques, while the estimated RMSE for measurements made by the non-modulated system is significantly higher. FIG. 8B illustrates a similar graph for measurements made in the presence of a 110 dB SPL 40 Hz interferer.

In some embodiments, measurement error may be caused by noise and interference that falls within the passband of bandpass filter 516 after being upconverted and/or downconverted by multiplier 522. Accordingly, in some embodiments, the bandwidth of bandpass filter 516 is made more narrow to filter out these disturbances. FIG. 8C illustrates a graph of estimated root mean square error RMSE vs estimated gas concentration for gas concentrations of 400 ppm, 1000 ppm, 2000 ppm and 4000 ppm in the presence of a 90 dB SPL 60 Hz interferer for an embodiment system that utilizes embodiment matched-filter techniques. Estimated root mean square error RMSE is shown for cases in which bandpass filter 516 has a passband from 35 Hz to 55 Hz; a passband from 35 Hz to 50 Hz; and a passband from 35 Hz to 45 Hz. As shown, lower estimated root mean square error RMSE is associated with narrower passbands.

Figure 9A:
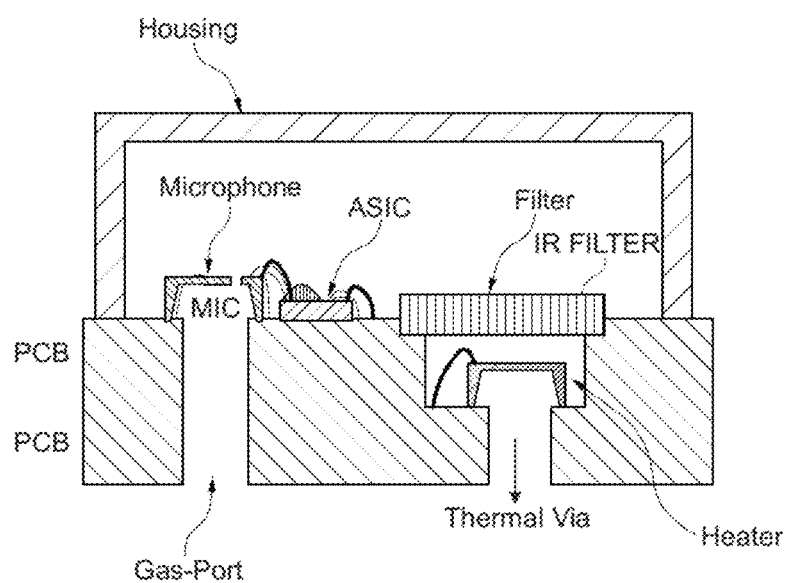
FIG. 9A illustrates a cross-section of an embodiment packaged photoacoustic gas sensing system.

FIG. 9A illustrates a cross section of an embodiment packaged photoacoustic gas sensor that may be used to implement embodiment photoacoustic gas sensors described above. As shown, the embodiment packaged photoacoustic gas sensor includes a printed circuit board (PCB) and a hollow housing disposed over the PCB. A microphone is disposed over a gas-port or cavity that is disposed within the PCB, an infrared light source (heater) is disposed over a thermal via disposed within the PCB, and an infrared filter is disposed between the infrared light source and the heater. An application specific integrated circuit (ASIC) that implements embodiment analysis systems is disposed on the PCB and is electrically connected to the microphone and the infrared light source. It should be appreciated that the package shown in FIG. 9A is just one of many possible system/package configurations that may be used to implement embodiment photoacoustic gas sensor systems.

Figure 9B:
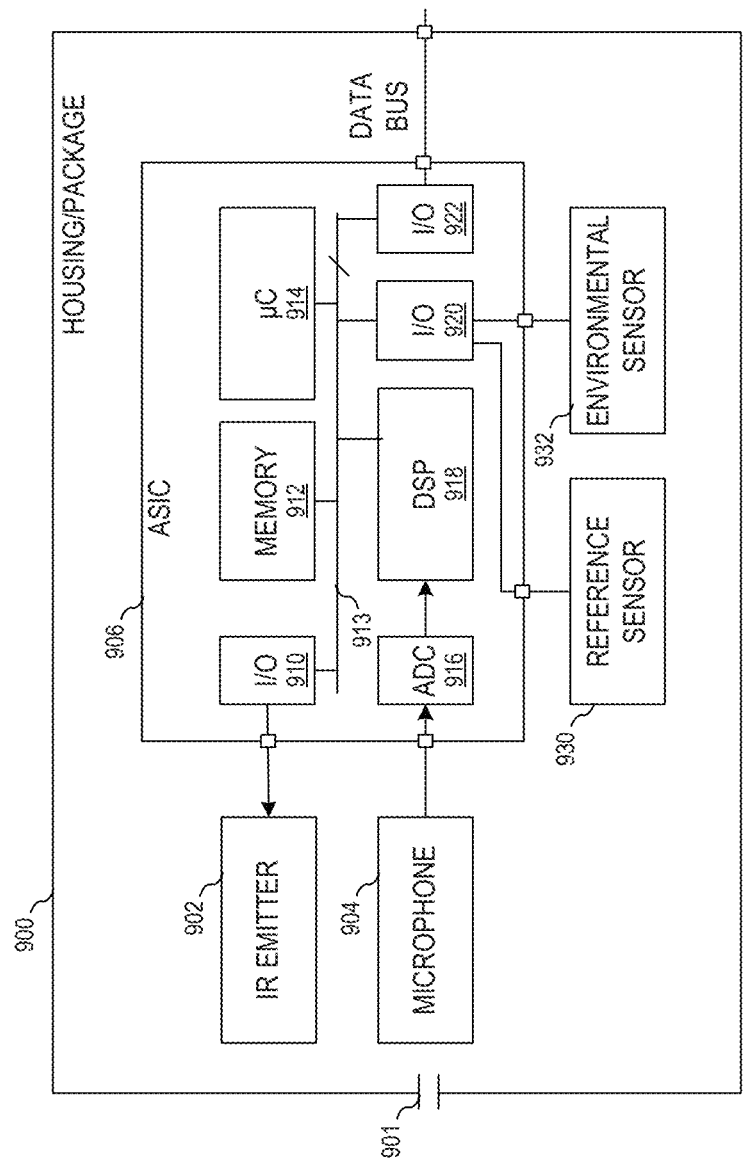
FIG. 9B illustrates a block diagram of an embodiment packaged photoacoustic gas sensing system.

FIG. 9B illustrates a block diagram of an embodiment system in a package 900 that may be used to implement embodiment photoacoustic gas sensors described above. As shown, package 900 includes port 901, infrared light source 902, microphone 904 and ASIC 906. In some embodiments, the system may also include a reference sensor 930 and one or more environmental sensors 932. ASIC 906 includes analog-to-digital converter 916 coupled to the output of microphone 904. Digital signal processor (DSP) 918 receives the output of ADC 916 and performs embodiment photoacoustic analysis methods described above. The overall operation of the photoacoustic system is controlled by microcontroller 914 that is coupled to DSP 918, I/O blocks 910, 920 and 922 and memory 912 via internal bus 913. Memory 912 may be used, for example, to store calibration parameters, intermediate measurement values, infrared light source modulation sequences, and the like. I/O block 910 is connected to infrared light source 902 and provides embodiment modulation signals thereto; I/O block 920 is connected to reference sensor 930 and environmental sensor 932; and I/O block 922 is connected to an external data bus or data interface that receives measurement requests and configuration information, as well as providing measurement results. Again, it should be appreciated that the package shown in FIG. 9B is just one of many possible system/package configurations that may be used to implement embodiment photoacoustic gas sensor systems.

FIGS. 10A-10E illustrate flow charts of embodiment photoacoustic calibration and estimation algorithms that may be used to the implement embodiment photoacoustic gas measurement systems described above. These methods describe steps that are performed during a calibration phase (carried out only once at the beginning or at given time instants) and the processing steps needed for the actual estimation of the gas concentration (e.g. every time a measurement is performed).

In a first approximation the raw microphone output signal at a generic time t, denoted as S(t, C,T,Pa,Rh), can be seen as the superimposition of two components: a photoacoustic part (PA) that is dependent on the gas concentration (C) and a thermo-acoustic part (TA) that is independent from the gas concentration. Both components depend on the temperature (T), pressure (PA) and humidity (Rh) of the surrounding environment. More specifically, $$S(t,C,T,Pa,Rh) = PA(t,C,T,Pa,Rh) + TA(t,T,Pa,Rh). \quad (7)$$

For C=0 ppm the photoacoustic part is ideally zero. Consequently, S(t,0,T,Pa,Rh) can be used to identify the thermo-acoustic component at a certain temperature T, pressure Pa and humidity Rh. However, in non-ideal situations, other noise components may be present in (7), such as white noise, acoustic disturbance, electrical coupling, etc.

Figures 10A, 10B, 10C:
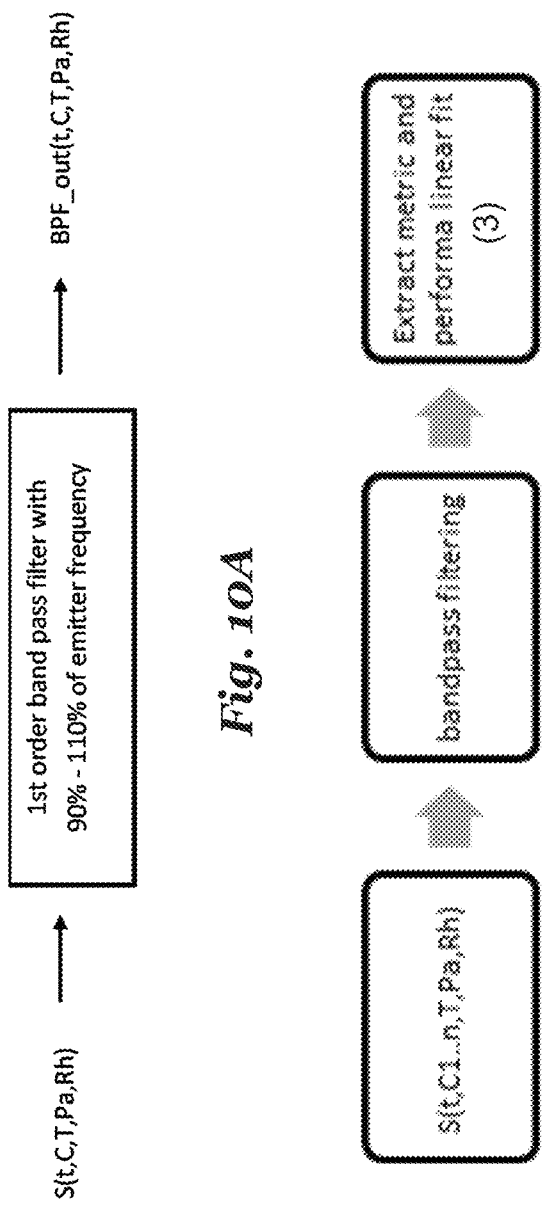

In an embodiment, as a first step common to embodiment algorithms for estimating the gas concentration is applying a bandpass filter (BPF) stage to the raw microphone output as illustrated in FIG. 10A. As shown, the microphone signal is filtered with a first order bandpass filter having a center frequency that is 90% to 100% of the emitter frequency, which is the frequency at which the infrared light source is modulated. In alternative embodiments, other the bandpass filters may have an order greater than one.

In some embodiments, an area under the curve (AUC) algorithm may be used in place of the IQ demodulation algorithm described above. In an embodiment, the area under the curve (AUC) is defined as:

$$AUC = \sqrt{\int_{t=t1}^{t2}(BPF_{out(t,C,T,pa,Rh)})^2}. \quad (8)$$

where BPF_out(t, C, T, Pa, Rh) is the output of the BPF. The value of AUC can be seen as the root of the mean value of the measurement signal BPF_out(t, C, T, Pa, Rh) squared. The outcome of this is the following estimation metric:

$$M_{est}(C) = \sqrt{\overline{(BPF_{out(t,C,T,Pa,Rh)})^2}}. \quad (9)$$

Calibration steps relating to the AUC algorithm are shown in FIG. 10B, and measurement/estimation steps are shown in FIG. 10C.

In a further embodiment, a K-slope algorithm may be used. For the K-slope algorithm, the slope at the minimum of the photoacoustic signal is calculated. A certain number of samples (e.g. 5) are taken around the intersection point. The intersection point is defined as:

$$t_{ip} = \min_t(|PA(t,C,T,Pa,Rh)|). \quad (10)$$

The metric is then extracted as:

$$K = \frac{BPF_{out(t,C,T,Pa,Rh)}(t_{ip} + 5T_{sa}) - BPF_{out(t,C,T,Pa,Rh)}(t_{ip} - 5T_{sa})}{10T_{sa}}. \quad (11)$$

where $T_{sa}$ is the sampling interval. Calibration steps relating to the K-slop algorithm are shown in FIG. 10D and measurement/estimation steps are shown in FIG. 10E.

Embodiment calibration and estimation algorithms may utilize various parameters of the photoacoustic signal produced by the microphone or pressure sensor. These parameters include, for example, sensitivity, range, precision, resolution, accuracy custom, linearity, SNR and TA/PA.

In an embodiment, the parameter of sensitivity is the slope of the output characteristic curve of the algorithm components, which may be expressed in LSB/ppm or AU/ppm:

$$Sensitivity = \frac{dy}{dx}. \quad (12)$$

A parameter of range (which may be expressed in ppm of LSM) is the maximum and minimum values of applied parameter that can be measured. Another parameter of precision is the degree of reproducibility of a measurement with the same environmental conditions. This may be expressed, for example, in ppm. The parameter of resolution, which may also be expressed in ppm, is the smallest change of the gas concentration input that can be detected on the output with the algorithm.

A parameter of accuracy custom, which may be expressed in ppm, is the absolute mean error difference that exists between the estimated gas concentration and the indicated value at the output of the sensor:

$$Accuracy = |real\ concentration - estimated\ concentration|. \quad (13)$$

A parameter of linearity, which may be expressed in % of full scale, is the difference between the estimated gas concentration and the indicated value at the output of the sensor.

A parameter of signal to noise ratio (SNR), in this case, is the ratio of photoacoustic power at a given concentration to the thermoacoustic ratio, which may be expressed as:

$$SNR = \frac{(BPF_{out(t,C1,T,Pa,Rh)} - TA)^2}{TA^2}. \quad (14)$$

Another parameter that could be used is the ratio between the thermo-acoustic (TA) response and the photoacoustic response (PA) of the system. The TA/PA parameter may be defined as the inverse of the square root of SNR value:

$$\frac{TA}{PA} = \sqrt{1/SNR}. \quad (15)$$

It should be understood that the parameters detailed above are just examples of many possible parameters that may be used by embodiment gas concentration estimation algorithms. Other parameters known in the art may also be used.

Example embodiments of the present invention are summarized here. Other embodiments can also be understood from the entirety of the specification and the claims filed herein.

Example 1

A method of measuring a gas concentration, the method including: modulating an infrared light source according to a frequency-hopped sequence including time intervals, where the infrared light source is modulated at a first frequency during a first time interval, the infrared light source is modulated as at second frequency during a subsequent time interval, and the first frequency is different from the second frequency; receiving a microphone signal from an output of a microphone acoustically coupled to a gas exposed to infrared light produced by the infrared light source; bandpass filtering the microphone signal using a bandpass filter to produce a filtered microphone signal; adjusting a center frequency of the bandpass filter according to the frequency-hopped sequence, where the bandpass filter includes a first center frequency corresponding to the first frequency during the first time interval, the bandpass filter includes a second center frequency corresponding to the second frequency during the subsequent time interval, where the first center frequency is different from the second center frequency; and estimating the gas concentration from the filtered microphone signal.

Example 2

The method of example 1, where estimating the gas concentration includes: performing a separate gas concentration estimate for each of the time intervals to produce a set of gas concentration estimates; determining which of the separate gas concentrations estimates are outlier estimates; removing the outlier estimates from the set of gas concentration estimates to form a revised set of gas concentration estimates; and determining the gas concentration based on the revised set of gas concentration estimates.

Example 3

The method of one of examples 1 or 2, where removing the outlier estimates includes determining a majority rule.

Example 4

The method of one of examples 1 to 3, where the bandpass filter includes a matched bandpass filter.

Example 5

The method of one of examples 1 to 4, further including calibrating the bandpass filter, calibrating including performing a test measurement corresponding to a first gas concentration, performing the test measurement including: modulating the infrared light source a test frequency; receiving the microphone signal; and storing a time response of the microphone signal corresponding to the test frequency.

Example 6

The method of one of examples 1 to 5, where the test frequency is a lowest frequency of the frequency-hopped sequence, and the first gas concentration corresponds to a lowest gas concentration.

Example 7

The method of one of examples 1 to 6, where bandpass filtering the microphone signal includes: shifting a frequency of the stored time response according to the adjusted center frequency of the bandpass filter to form a shifted time response; and convolving the shifted time response with the received microphone signal.

Example 8

The method of one of examples 1 to 7, where: shifting the frequency of the stored time response includes shifting an FFT of the stored time response; and convolving the shifting time response with the received microphone signal includes multiplying an FFT of the received microphone signal with the shifted FFT of the stored time response.

Example 9

The method of one of examples 1 to 8, where estimating the gas concentration from the filtered microphone signal includes applying a linear fit model to the filtered microphone signal.

Example 10

A system for measuring a gas concentration including: an analysis circuit having a modulation output configured to be coupled to an input of an infrared light source, and bandpass filter having an input configured to be electrically coupled to an output of a microphone, where the analysis circuit is configured to modulate the infrared light source via the modulation output according to a frequency-hopped sequence including time intervals by modulating the infrared light source at a first frequency during a first time interval and at a second frequency different from the first frequency during a subsequent time interval, adjust a center frequency of the bandpass filter according to the frequency-hopped sequence, where the bandpass filter includes a first center frequency corresponding to the first frequency during the first time interval and a second center frequency different from the first center frequency, the second center frequency corresponding to the second frequency during the subsequent time interval, and estimate the gas concentration based on an output of the bandpass filter.

Example 11

The system of example 10, where the analysis circuit is disposed on a single integrated circuit.

Example 12

The system of one of examples 10 or 11, further including the infrared light source and the microphone, where the microphone is acoustically coupled to a gas exposed to infrared light produced by the infrared light source.

Example 13

The system of one of examples 10 to 12, where the microphone is a MEMS microphone.

Example 14

A method of measuring a gas concentration, the method including: modulating an infrared light source according to a pulse sequence; receiving a microphone signal from an output of a microphone acoustically coupled to a gas exposed to infrared light produced by the infrared light source; multiplying the received microphone signal with a matched signal corresponding to the pulse sequence to form a despreaded microphone signal; bandpass filtering the despreaded microphone signal to form a bandpass filtered despreaded microphone signal; and estimating the gas concentration from the bandpass filtered despreaded microphone signal.

Example 15

The method of example 14, further including calibrating the matched signal, calibrating including performing a test measurement corresponding to a first gas concentration, performing the test measurement including: modulating the infrared light source according to a calibration pulse; receiving the microphone signal; and storing a time response of the microphone signal corresponding to the calibration.

Example 16

The method of one of examples 14 or 15, where multiplying the received microphone signal with the matched signal corresponding to the pulse sequence including multiplying the received microphone signal with the stored time response of the microphone signal corresponding to the calibrating.

Example 17

The method of one of examples 14 to 16, where estimating the gas concentration from the bandpass filtered despreaded microphone signal includes applying a linear fit model to the bandpass filtered despreaded microphone signal.

Example 18

A system for measuring a gas concentration including: an analysis circuit having a modulation output configured to be coupled to an input of an infrared light source, and a microphone input configured to be electrically coupled to an output of a microphone, where the analysis circuit is configured to modulate the infrared light source via the modulation output according to a pulse sequence; multiply a microphone signal received at the output of the microphone with a matched signal corresponding to the pulse sequence to form a despreaded microphone signal; bandpass filter the despreaded microphone signal to form a bandpass filtered despreaded microphone signal; and estimate the gas concentration from the bandpass filtered despreaded microphone signal.

Example 19

The system of example 18, where the analysis circuit is disposed on a single integrated circuit.

Example 20

The system of one of examples 18 or 19, further including the infrared light source and the microphone, where the microphone is acoustically coupled to a gas exposed to infrared light produced by the infrared light source.

Example 21

The system of one of examples 18 to 20, where the microphone is a MEMS microphone.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method of measuring a gas concentration, the method comprising:
    modulating an infrared light source according to a pulse sequence;
    receiving a microphone signal from an output of a microphone acoustically coupled to a gas exposed to infrared light produced by the infrared light source;
    multiplying the received microphone signal with a matched signal corresponding to the pulse sequence to form a despreaded microphone signal;
    bandpass filtering the despreaded microphone signal to form a bandpass filtered despreaded microphone signal; and
    estimating the gas concentration from the bandpass filtered despreaded microphone signal.

2. The method of claim 1, further comprising calibrating the matched signal, calibrating comprising performing a test measurement corresponding to a first gas concentration, performing the test measurement comprising:
    modulating the infrared light source according to a calibration pulse;
    receiving the microphone signal; and
    storing a time response of the microphone signal corresponding to the calibration pulse.

3. The method of claim 2, wherein multiplying the received microphone signal with the matched signal corresponding to the pulse sequence comprises multiplying the received microphone signal with the stored time response of the microphone signal corresponding to the calibrating.

4. The method of claim 2, wherein performing the test measurement further comprises performing a preliminary calibration measurement in a presence of a preliminary gas concentration, wherein the preliminary gas concentration is less than the first gas concentration.

5. The method of claim 2, wherein performing the test measurement further comprises performing a plurality of test measurements corresponding to a plurality of different gas concentrations.

6. The method of claim 1, wherein estimating the gas concentration from the bandpass filtered despreaded microphone signal comprises applying a linear fit model to the bandpass filtered despreaded microphone signal.

7. The method of claim 1, further comprising generating the pulse sequence, wherein the pulse sequence comprises a variable distance between pulses of the pulse sequence.

8. A system for measuring a gas concentration comprising:
an analysis circuit having a modulation output configured to be coupled to an input of an infrared light source, and a microphone input configured to be electrically coupled to an output of a microphone, wherein the analysis circuit is configured to
modulate the infrared light source via the modulation output according to a pulse sequence;
multiply a microphone signal received at the output of the microphone with a matched signal corresponding to the pulse sequence to form a despreaded microphone signal;
bandpass filter the despreaded microphone signal to form a bandpass filtered despreaded microphone signal; and
estimate the gas concentration from the bandpass filtered despreaded microphone signal.

9. The system of claim 8, wherein the analysis circuit is disposed on a single integrated circuit.

10. The system of claim 8, further comprising the infrared light source and the microphone, wherein the microphone is acoustically coupled to a gas exposed to infrared light produced by the infrared light source.

11. The system of claim 10, wherein the microphone is a MEMS microphone.

12. The system of claim 8, wherein the analysis circuit is further configured to calibrate the matched signal by performing a test measurement corresponding to a first gas concentration, wherein performing the test measurement comprises:
modulating the infrared light source according to a calibration pulse;
receiving the microphone signal; and
storing a time response of the microphone signal corresponding to the calibration pulse.

13. The system of claim 12, wherein the analysis circuit is configured to multiply the received microphone signal with the matched signal corresponding to the pulse sequence by multiplying the received microphone signal with the stored time response of the microphone signal corresponding to the calibrating.

14. The system of claim 8, wherein the analysis circuit is configured to estimate the gas concentration from the bandpass filtered despreaded microphone signal by applying a linear fit model to the bandpass filtered despreaded microphone signal.

15. The system of claim 8, wherein the pulse sequences comprises a variable distance between pulses of the pulse sequence, and the variable distance is according to a known sequence of $\{\tau_i\}_{i=1, \ldots, N_p}$ of period $N_p$.

16. A gas concentration measurement system comprising:
a housing comprising a gas port and a thermal via;
a microphone in the housing disposed over the gas port;
an heater disposed in the housing over the thermal via; and
an integrated circuit disposed in the housing, the integrated circuit having a modulation output coupled to an input of the heater, and a microphone input electrically coupled to an output of the microphone, wherein the integrated circuit comprises a processor configured to:
generate a pulse sequence and a matching signal corresponding to the pulse sequence,
provide the pulse sequence to the heater via the modulation output,
multiply a microphone signal received via the microphone input a matched signal corresponding to the pulse sequence to form a despreaded microphone signal,
bandpass filter the despreaded microphone signal to form a bandpass filtered despreaded microphone signal, and
estimate the gas concentration from the bandpass filtered despreaded microphone signal to provide a gas concentration measurement.

17. The system according to claim 16, further comprising an infrared filter disposed adjacent to the heater.

18. The system according to claim 16, further comprising at least one environmental sensor disposed within the housing and electrically coupled to the integrated circuit, wherein the at least one environmental sensor comprises at least one of a temperature sensor, humidity sensor or a pressure sensor, and the processor is configured to adjust the gas concentration measurement according to a measurement performed by the at least one environmental sensor.

19. The system according to claim 16, wherein the processor is further configured to calibrate the matched signal by performing a test measurement corresponding to a first gas concentration by:
providing a calibration pulse to the heater;
receiving the microphone signal; and
storing a time response of the microphone signal corresponding to the calibration pulse.

20. The system of claim 19, wherein the processor is further configured to multiply the received microphone signal with the matched signal corresponding to the pulse sequence by multiplying the received microphone signal with the stored time response.

* * * * *